United States Patent
Wada et al.

(10) Patent No.: US 10,852,308 B2
(45) Date of Patent: Dec. 1, 2020

(54) DISEASE-STATE BIOMARKER FOR RENAL DISEASE

(71) Applicants: Kanazawa University, Kanazawa-shi, Ishikawa (JP); Kagami Inc., Ibaraki-shi (JP)

(72) Inventors: Takashi Wada, Ishikawa (JP); Kengo Furuichi, Ishikawa (JP); Norihiro Sakai, Ishikawa (JP); Yasunori Iwata, Ishikawa (JP); Akinori Hara, Ishikawa (JP); Yusuke Nakade, Ishikawa (JP); Kenji Hamase, Fukuoka (JP); Yurika Miyoshi, Fukuoka (JP); Maiko Nakane, Tokyo (JP); Masashi Mita, Tokyo (JP)

(73) Assignees: Kanazawa University, Ishikawa (JP); Kagami, Inc., Osaka (JP)

( * ) Notice: Subject to any disclaimer, the term of this patent is extended or adjusted under 35 U.S.C. 154(b) by 269 days.

(21) Appl. No.: 15/580,855

(22) PCT Filed: Jun. 10, 2016

(86) PCT No.: PCT/JP2016/067459
§ 371 (c)(1),
(2) Date: Dec. 8, 2017

(87) PCT Pub. No.: WO2016/199928
PCT Pub. Date: Dec. 15, 2016

(65) Prior Publication Data
US 2018/0252730 A1 Sep. 6, 2018

(30) Foreign Application Priority Data
Jun. 10, 2015 (JP) ................. 2015-117881

(51) Int. Cl.
*G01N 33/00* (2006.01)
*G01N 33/68* (2006.01)

(52) U.S. Cl.
CPC ..... *G01N 33/6893* (2013.01); *G01N 33/6806* (2013.01); *G01N 2800/347* (2013.01)

(58) Field of Classification Search
CPC ................................................. G01N 33/6893
(Continued)

(56) References Cited

U.S. PATENT DOCUMENTS

2015/0079623 A1  3/2015  Hamase et al.

FOREIGN PATENT DOCUMENTS

| EP | 2468888 A1 | 6/2012 |
| JP | 09-110707 A1 | 4/1997 |
| JP | 2013-224929 A | 10/2013 |

OTHER PUBLICATIONS

Abstracts, "9th International Congress on Amino Acids and Proteins," Vienna, Austria, Aug. 8-12, 2005, Amino Acids, 2005, 29(1):1-77.
(Continued)

*Primary Examiner* — Christopher Adam Hixson
*Assistant Examiner* — Emily R. Berkeley
(74) *Attorney, Agent, or Firm* — Foley & Lardner LLP

(57) ABSTRACT

The present invention addresses the problem of developing an analytical method which makes it possible to diagnose early or mild renal disorders. The method is based on calculating a disease-state index value for renal disorders on the basis of the quantities of D-form and/or L-form amino acids, from feces or intestinal content. By comparing the disease-state index value with a threshold value determined from the disease-state index values of a renal failure patient group and a healthy subject group, it is possible to diagnose a mild renal disorder patient group.

9 Claims, 19 Drawing Sheets

(58) Field of Classification Search
USPC .......................................................... 436/90
See application file for complete search history.

(56) References Cited

OTHER PUBLICATIONS

Abe, Ryuzo, "Byotai ni Ojita Eiyo o Kangaeyoi Kyusei Jinfuzen Kanja," Emerg. Care, 2008, New Year special extra issue, 211-217.
Brueckner et al., "Gas chromatographic characterization of free D-amino acids in the blood serum of patients with renal disorders and of healthy volunteers," Journal of Chromatography, 1993, 614(1):7-17.
Furutani, Jun'ya, "Mansei Jinfuzenji ni Okeru Chokan Peptide Oyobi, Amino-san Yuso Kiko no Kaiseki," Amino Acid Research, 2007, 1(1):70-71.
Kawashima, Akira, "Mansei Jinfuzen no Subete 2000 Choki Toseki Gappeisho Guhatsusho no Byotai to Chiryo Taishakei Tanpakushitsu Amino-san Taisha Ijo," Kidney and Dialysis, 2000, 49(special extra):817-820.
Lu et al., "Metabonomic study on 'Kidney-Yang Deficiency syndrome' and intervention effects of Rhizoma Drynariae extracts in rats using ultra performance liquid chromatography coupled with mass spectrometry," Talanta, 2011, 83(3);700-708.
Nagata et al., "D-Amino acids in mouse tissues are not of microbial origin," Experientia, 1990, 46(5):466-468.
Tsubakihara, Yoshiharu, "V. Iji Ketsueki Toseki Ryoho Nyodokusho no Byotairon Tanpakushitsu Amino-san Taisha Ijo," Japanese Journal of Clinical Medicine, 2004, 62(special extra 6):124-135.
Fukushima et al., "Determination of D-Amino Acids in Serum from Patients with Renal Dysfunction," Biol. Pharm. Bull., Aug. 1995, 18(8):1130-1132.
Furutani, Jun'ya, "Analysis of the Intestinal Peptide and Amino Acid Transport Mechanism during chronic Renal Failure," Amino Acid Research, 2007, 1(1):70-71, English translation, 2 pages.
Huang et al., "Urinary Excretion of D-Serine in Human: Comparison of Different Ages and Species," Biol. Pharm. Bull., Feb. 1998, 21(2):156-162.
Ishida, Hironori, "Serum D-Amino Acid Elucidated in Renal Failure," Kitasato Med., 1993, 23:51-62, with English abstract on last page.
Kawashima, Akira, "V. Pathology and Treatment of Long-Term Dialysis Complications and Accidents, 220. Disorders of Protein and Amino Acid Metabolism," Kidney and Dialysis, Nov. 30, 2000, 49(special extra):817-820, English translation, 6 pages.
KDIGO 2012 Clinical Practice Guideline for the Evaluation and Management of Chronic Kidney Disease, Kidney International Supplements, Jan. 2013, 3(1), 162 pages.
Nagata, Yoko, "Neutral free D-amino acids present in human plasma," Viva Origino, Jul. 19, 1990, 18(2):88-89, with English translation, 2 pages.
Slocum et al., "Marking renal injury: can we move beyond serum creatinine?", Transl. Res., Apr. 2012, 159:277-289.
Tsubakihara, Yoshiharu, "Protein and amino acid metabolism disorders" Japanese Journal of Clinical Medicine, Jun. 28, 2004, 62(special extra 6):124-135, English translation, 2 pages.

(A)

Kidney disorder induction group (B)

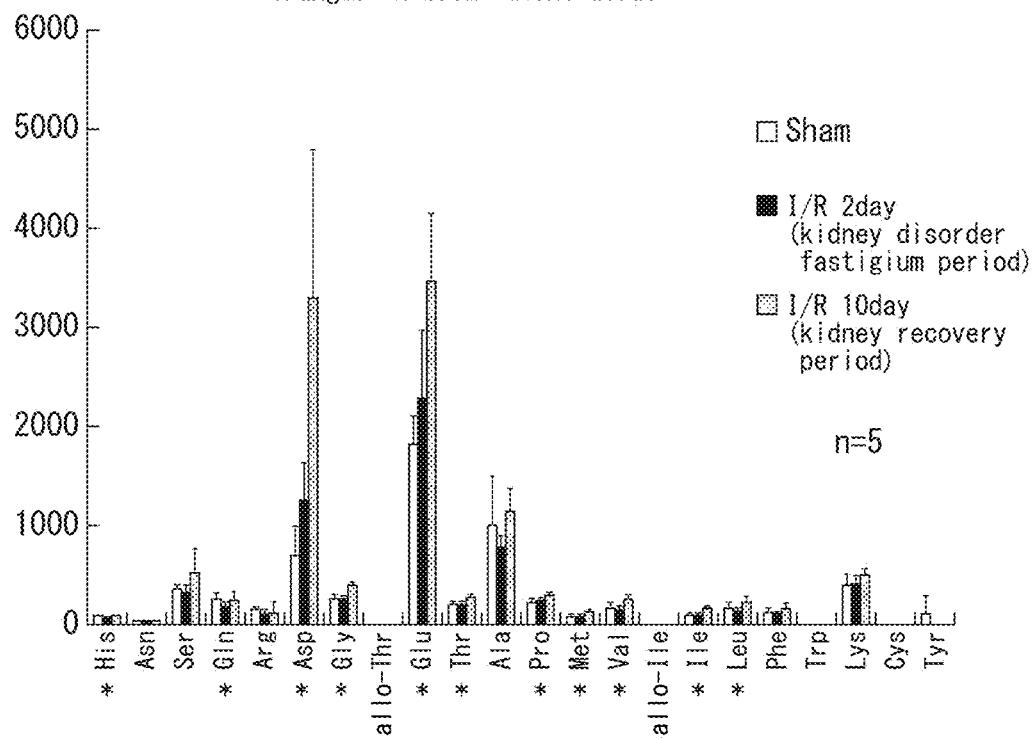
FIG. 3(A) Changes in total amino acids
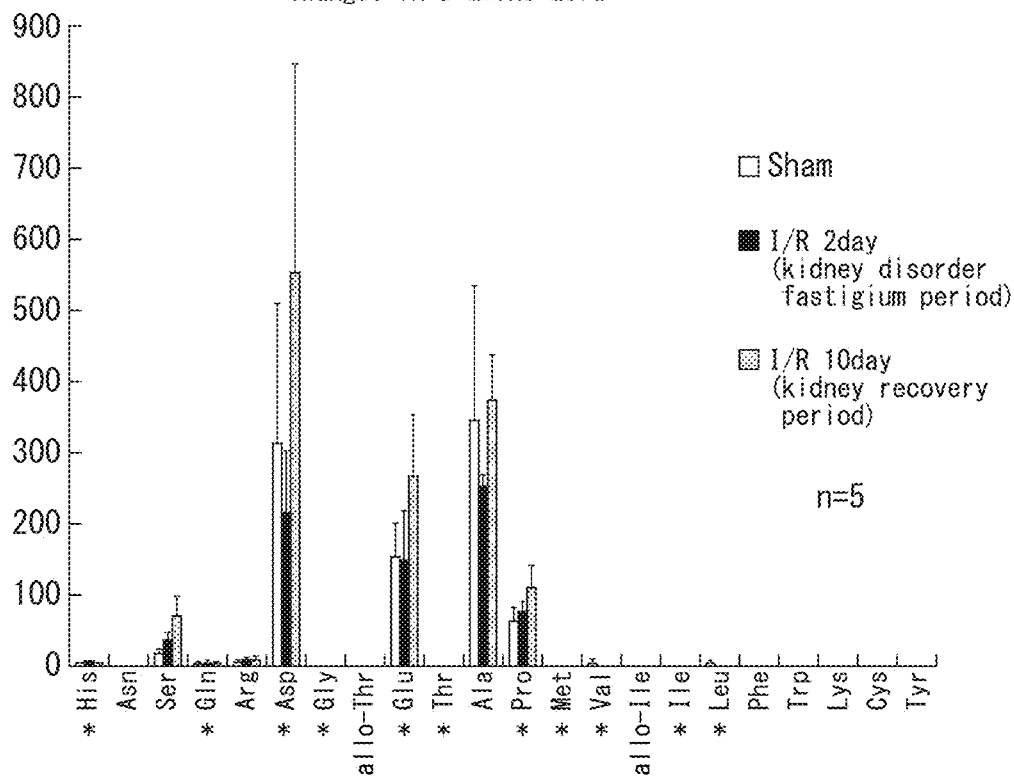
FIG. 3(B) Changes in D-amino acid

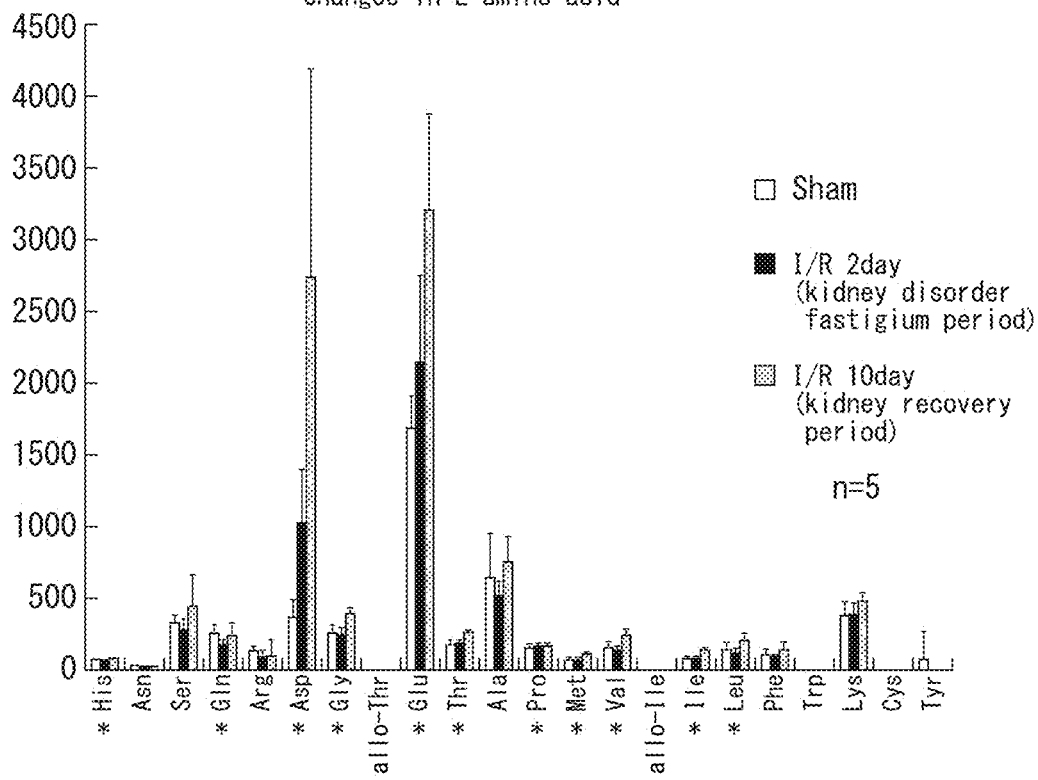
FIG. 3(C) Changes in L-amino acid
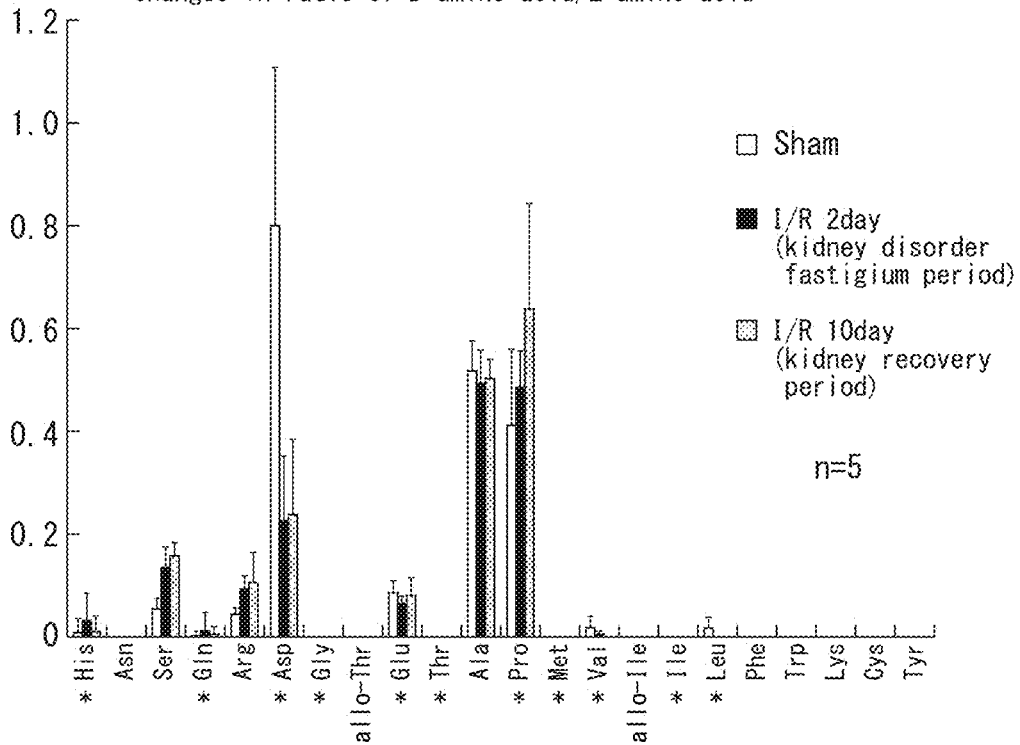
FIG. 3(D) Changes in ratio of D-amino acid/L-amino acid

FIG. 3(F)
Significant Difference Table

| | D | | | L | | | D+L | | | D/L | | | D/(D+L) | | |
|---|---|---|---|---|---|---|---|---|---|---|---|---|---|---|---|
| | sham vs 1/R2days | 1/R2days vs 1/R10days | sham vs 1/R10days | sham vs 1/R2days | 1/R2days vs 1/R10days | sham vs 1/R10days | sham vs 1/R2days | 1/R2days vs 1/R10days | sham vs 1/R10days | sham vs 1/R2days | 1/R2days vs 1/R10days | sham vs 1/R10days | sham vs 1/R2days | 1/R2days vs 1/R10days | sham vs 1/R10days |
| His | | | | ** | | | | | | | | | | | |
| Asn | *** | | | | | | | | | | | | | | |
| Ser | *** | * | ** | | | | ** | | *** | ** | | *** | ** | | *** |
| Gln | | | | | | | * | | | | | | | | |
| Arg | | | | | | | * | | * | * | | ** | ** | | * |
| Asp | | * | ** | *** | ** | ** | ** | | ** | *** | | *** | *** | | *** |
| Gly | <LOQ | <LOQ | <LOQ | *** | *** | <LOQ | <LOQ | <LOQ | <LOQ | <LOQ | <LOQ | <LOQ | <LOQ | <LOQ | <LOQ |
| allo-Thr | <LOQ | <LOQ | <LOQ | <LOQ | <LOQ | <LOQ | <LOQ | <LOQ | <LOQ | <LOQ | <LOQ | <LOQ | <LOQ | <LOQ | <LOQ |
| Glu | <LOQ | <LOQ | <LOQ | *** | *** | *** | * | | | <LOQ | <LOQ | <LOQ | <LOQ | <LOQ | <LOQ |
| Thr | | * | | *** | | | | | | <LOQ | <LOQ | <LOQ | <LOQ | <LOQ | <LOQ |
| Ala | <LOQ | *** | | | | ** | <LOQ | <LOQ | <LOQ | <LOQ | <LOQ | <LOQ | <LOQ | <LOQ | <LOQ |
| Pro | <LOQ | | * | | | * | <LOQ | * | <LOQ | <LOQ | <LOQ | <LOQ | <LOQ | <LOQ | <LOQ |
| Met | <LOQ | <LOQ | <LOQ | ** | ** | <LOQ | <LOQ | *** | <LOQ | <LOQ | <LOQ | <LOQ | <LOQ | <LOQ | <LOQ |
| Val | <LOQ | <LOQ | <LOQ | *** | *** | <LOQ | <LOQ | <LOQ | <LOQ | <LOQ | <LOQ | <LOQ | <LOQ | <LOQ | <LOQ |
| allo-Ile | <LOQ | <LOQ | <LOQ | *** | | <LOQ | <LOQ | <LOQ | <LOQ | <LOQ | <LOQ | <LOQ | <LOQ | <LOQ | <LOQ |
| Ile | <LOQ | <LOQ | <LOQ | * | | <LOQ | <LOQ | <LOQ | <LOQ | <LOQ | <LOQ | <LOQ | <LOQ | <LOQ | <LOQ |
| Leu | * | | <LOQ | | | | <LOQ | | <LOQ | <LOQ | <LOQ | <LOQ | * | * | * |
| Phe | <LOQ | <LOQ | <LOQ | | | | <LOQ | <LOQ | <LOQ | <LOQ | <LOQ | <LOQ | <LOQ | <LOQ | <LOQ |
| Trp | <LOQ | <LOQ | <LOQ | | | | <LOQ | <LOQ | <LOQ | <LOQ | <LOQ | <LOQ | <LOQ | <LOQ | <LOQ |
| Lys | <LOQ | <LOQ | <LOQ | | | | <LOQ | <LOQ | <LOQ | <LOQ | <LOQ | <LOQ | <LOQ | <LOQ | <LOQ |
| Cys | <LOQ | <LOQ | <LOQ | | | | <LOQ | <LOQ | <LOQ | <LOQ | <LOQ | <LOQ | <LOQ | <LOQ | <LOQ |
| Tyr | <LOQ | <LOQ | <LOQ | | | | <LOQ | <LOQ | <LOQ | <LOQ | <LOQ | <LOQ | <LOQ | <LOQ | <LOQ |

\* $P<0.05$
\*\* $P<0.01$
\*\*\* $P<0.005$ (A)

Wild group     Sterile group     Inoculated group (B)

(A)

(B)

Total amino acids

L-amino acids

D-amino acids

Ratio of D-amino acid/L-amino acid

FIG. 11

|  | Total amino acid | | L-amino acid | | D-amino acid | | D/L amino acid | |
| --- | --- | --- | --- | --- | --- | --- | --- | --- |
|  | r | p | r | p | r | p | r | p |
| His | 0.837 | | 0.836 | | 0.804 | | 0.804 | |
| Asn | -0.505 | | -0.505 | | 0.000 | | 0.000 | |
| Ser | -0.143 | | -0.146 | | -0.059 | | 0.095 | |
| Gln | -0.188 | | -0.188 | | 0.000 | | 0.000 | |
| Arg | -0.528 | | -0.528 | | 0.000 | | 0.000 | |
| Asp | -0.209 | | -0.264 | | -0.032 | | 0.522 | |
| Gly | -0.156 | | -0.156 | | 0.000 | | 0.000 | |
| allo-Thr | 0.804 | | 0.000 | | 0.804 | | 0.000 | |
| Glu | -0.117 | | -0.117 | | -0.110 | | -0.148 | |
| Thr | -0.170 | | -0.170 | | 0.000 | | 0.000 | |
| Ala | 0.122 | | 0.215 | | -0.063 | | -0.543 | |
| Pro | 0.050 | | -0.013 | | 0.125 | | 0.564 | |
| Met | -0.210 | | -0.210 | | 0.000 | | 0.000 | |
| Val | -0.257 | | -0.257 | | -0.023 | | 0.401 | |
| allo-Ile | -0.460 | | 0.000 | | -0.460 | | 0.000 | |
| Ile | -0.295 | | -0.295 | | 0.000 | | 0.000 | |
| Leu | -0.322 | | -0.314 | | -0.422 | | -0.109 | |
| Phe | -0.475 | | -0.475 | | -0.510 | | -0.437 | |
| Trp | 0.000 | | 0.000 | | 0.000 | | 0.000 | |
| Lys | 0.277 | | 0.507 | | -0.703 | | -0.844 | |
| Cys | 0.000 | | 0.000 | | 0.000 | | 0.000 | |
| Tyr | -0.342 | | -0.342 | | 0.000 | | 0.000 | |

Patient with CDK (PD) n = 8

DISEASE-STATE BIOMARKER FOR RENAL DISEASE

CROSS-REFERENCE TO RELATED APPLICATIONS

This application is a National Stage application of PCT/JP2016/067459, filed Jun. 10, 2016, which claims priority from Japanese application JP 2015-117881, filed Jun. 10, 2015.

TECHNICAL FIELD

The present invention relates to an analytical method, a kidney disorder testing method, and a sample analysis system for outputting pathological information regarding a kidney disorder, comprising a step for calculating a disease-state index value of a kidney disorder based on the amounts of D-form and L-form amino acids present in feces or intestinal content.

BACKGROUND ART

The kidney is an organ that fulfills the major role of maintaining homeostasis of body fluids by filtering waste products and excess water from the blood and excreting as urine. The kidney is affected by factors such as immune system abnormalities or drug allergies, hypertension, diabetes, hemorrhage or sudden drops in blood pressure, infections or dehydration associated with burns, and these factors result in decreased kidney function. Cases in which kidney function has decreased to 60% or lower due to a kidney disorder is referred to as kidney failure, and this is classified as acute kidney injury (AKI) or chronic kidney disease (CKD) according to differences in the rate of progression of the decrease in kidney function.

Acute kidney injury (AKI) refers to kidney failure for which the amount of time that has elapsed since onset is from several hours to several weeks. Acute kidney injury is a state in which kidney function has decreased suddenly due to such factors as ischemia, drugs or endotoxin shock, presents with elevated blood concentrations of urea nitrogen and creatinine, which are internal metabolites, abnormal electrolyte metabolism or symptoms of acidosis, and is typically diagnosed as acute kidney injury based on a sudden rise in serum creatinine level. Since patients are expected to recover from acute kidney injury with treatment, there is a desire for the development of a diagnostic marker capable of identifying acute kidney injury at an early stage. However, since commonly used serum creatinine concentration fluctuates according to conditions such as age, gender, muscle mass or medicines taken, this cannot be said to be a specific diagnostic marker (Non-Patent Document 1), and although proteins, such as neutrophil gelatinase-associated lipocalin (NGAL), interleukin-18 (IL-18), kidney injury molecule-1 (KIM-1), liver fatty acid-bonding proteins (FABPs) or cystatin C, and low molecular weight metabolic compounds, such as homovanillic Acid Sulfate, trymethyl-amine-N-oxide, etc., have been reported for use as diagnostic markers, the development of a diagnostic marker capable of detecting disease more rapidly and more accurately is still awaited.

Chronic kidney disease (CKD) refers to kidney failure in which decreases in kidney function, as represented by glomerular filtration rate, or findings suggestive of injury of kidney persist chronically (for 3 months or longer). Chronic kidney disease is a disease that currently affects 13.3 million Japanese, equivalent to about 13% of the total adult Japanese population, and has a high risk of leading to end stage kidney disease (ESKD), thereby resulting in a considerable threat to health. There is currently no effective method of treatment for chronic kidney disease, and since the progression of chronic kidney disease and the continued decrease in kidney function leads to risk of uremia resulting in the need for artificial dialysis or kidney transplant, the resulting medical economic burden is considerable (Non-Patent Document 2). Since chronic kidney disease progresses in the absence of subjective symptoms, diagnosis using early diagnostic markers for kidney failure is required for early detection and inhibition of the progression of chronic kidney disease. However, there are currently no diagnostic markers that are satisfactory in terms of accurately reflecting the progression of kidney disorder at an earlier stage than the occurrence of changes in kidney function capable of being detected by glomerular filtration rate.

In both the cases of acute kidney injury and chronic kidney disease, it is thought that an undamaged glomerulus is able to demonstrate sufficient kidney function (namely, the function of filtering waste products and excess water from the blood) by functioning at least at the normal level thereof up until kidney function has been impaired to a certain degree, such as by about 30%, in the case of the kidneys having been damaged due to the unavailability of an early diagnostic marker. Although creatinine and blood urea nitrogen (BUN), which are waste products excreted into urine, are used as kidney failure markers, up until the point at which kidney function is lost to a certain degree, there are no increases in creatinine and BUN levels in the blood since these waste products are normally excreted into urine. Although recently developed markers such as NGAL or KIM-1 are expected to serve as diagnostic markers since they are proteins expressed by inflammatory cells, there are currently no markers capable of satisfying the requirements described above.

D-amino acids, which were previously thought to not be present in mammalian body, have been determined to be present in various tissues, and are predicted to be responsible in some way for physiological function. In addition, concentrations of the D-amino acids of D-serine, D-alanine, D-proline, D-serine, D-glutamic acid and D-arachidonic acid present in serum have been indicated to be able to function as diagnostic markers of kidney failure (Non-Patent Document 3, Non-Patent Document 4, Non-Patent Document 5 and Non-Patent Document 6). Moreover, one type or two or more types of amino acids selected from the group consisting of D-serine, D-threonine, D-alanine, D-asparagine, D-allo-threonine, D-glutamine, D-proline and D-phenylalanine have been disclosed to be able to serve as disease-state index values of kidney disease (Patent Document 1), and although this publication lists body fluids such as blood, plasma or urine, excretions such as feces, sweat or nasal discharge, and body tissue such as body hair, nails, skin tissue or organ tissue as biological materials used for samples, there is no indication whatsoever of the actual use of D-form amino acids present in feces as diagnostic markers.

PRIOR ART DOCUMENTS

Patent Documents

Patent Document 1: International Publication No. WO 2013/140785

Non-Patent Documents

Non-Patent Document 1: Slocum, J. L., et al, Transl. Res., 159: 277 (2012)

Non-Patent Document 2: KDIGO 2012: Clinical Practice Guidelines for the Evaluation and Management of Chronic Kidney Disease, Kidney International Supplements, 1 (2013)

Non-Patent Document 3: Fukushima, T., et al, Biol. Pharm. Bull., 18: 1130 (1995)

Non-Patent Document 4: Nagata, Y., Viva Origino Vol. 18 (No. 2) (1990), Collection of Lecture Abstracts of the 15th Academic Symposium Non-Patent Document 5: Ishida, et al, Kitosato Medical Journal, 23: 51-62 (1993)

Non-Patent Document 6: Yong Huang, et al, Biol. Pharm. Bull., 21: (2), 156-162 (1998)

DISCLOSURE OF THE INVENTION

Problems to be Solved by the Invention

There is a desire to develop a technology for identifying and analyzing a diagnostic marker for kidney failure that fluctuates at an earlier stage than existing diagnostic markers for kidney failure such as glomerular filtration rate or serum creatinine concentration, and to develop a technology for accurately assessing, testing or diagnosing early kidney disease using that technology.

Means for Solving the Problems

The inventors of the present invention searched for an early diagnostic marker for kidney failure using an experimental animal model of early kidney disorder capable of reproducing early kidney failure. More specifically, the inventors of the present invention induced an ischemic kidney disorder in mice by clipping the kidney artery and kidney vein. A mild kidney disorder experimental animal model was thus produced in which, although the onset of inflammation can be confirmed in kidney tissue of the ischemic kidney disorder-induced mice (FIGS. 1 and 2), the levels of commonly used kidney disorder diagnostic markers consisting of serum creatinine concentration, KIM-1 and NGAL do not change. As a result, the levels of D-amino acids in feces were found to change in the mild kidney disease/injury experimental animal model (FIGS. 3 and 4). These newly discovered changes in D-amino acid levels in feces were confirmed to be involved in kidney disorder, thereby leading to completion of the present invention.

Moreover, as a result of measuring levels of D-form and L-form amino acids in the feces of a chronic kidney disease patient group and healthy subject group, the inventors of the present invention found that several chiral amino acids fluctuated significantly in the chronic kidney disease patient group in comparison with the healthy subject group, thereby leading to completion of the present invention.

Thus, the present invention relates to a method for analyzing feces or intestinal content, comprising:

a step for measuring the amounts of the D-form and/or L-form of at least one amino acid, and a step for calculating a disease-state index value of a kidney disorder based on the amount of the D-form, the amount of the L-form, or the amount of the D-form and L-form, of the at least one type of amino acid.

In another aspect thereof, the present invention relates to a method for testing for a kidney disorder by using feces or intestinal content as a sample, further comprising:

a step for measuring the amounts of the D-form and/or L-form of at least one amino acid, and a step for calculating a disease-state index value of a kidney disorder based on the amount of the D-form, the amount of the L-form, or the amount of the D-form and L-form, of the at least one type of amino acid; and a step for correlating the disease-state index value of the kidney disorder with the pathology of the kidney disorder. This testing method can be used to determine the pathology of a kidney disorder based on a predetermined threshold value of the disease-state index value.

In still another aspect thereof, the present invention relates to a sample analysis system capable of carrying out the analytical method of the present invention. This sample analysis system includes a storage unit, input unit, analysis and measurement unit, data processing unit and pathological information output unit, and is capable of outputting pathological information by analyzing a sample of feces or intestinal content.

In still another aspect thereof, the present invention relates to program capable of being installed in the sample analysis system of the present invention, and a storage medium for containing that program.

Effects of the Invention

A disease-state index value, calculated based on the amount of a D-amino acid, L-amino acid or the amount of a D-amino acid and L-amino acid in a sample consisting of feces or intestinal content, enables the detection of kidney failure by a mechanism of action that differs from that of known kidney failure markers such as blood creatinine. As a result, it has the potential to be able to be used as a diagnostic marker capable of detecting kidney failure at an earlier stage than known markers such as blood creatinine. In addition, the feces or intestinal content used as sample can be acquired easily and non-invasively. Since this diagnostic marker enables early detection of kidney failure and the sample can be acquired easily, the use of the analytical method of the present invention in diagnosis enables early detection of kidney failure and/or kidney disorder.

BRIEF DESCRIPTION OF THE DRAWINGS

FIG. 3(A) is a graph indicating fluctuations in the total amounts of D-amino acids and L-amino acids present in feces sampled from mice of a control group (sham) and mice on days 2 and 10 following induction of a kidney disorder. FIG. 3(B) is a graph indicating fluctuations in the amounts of D-amino acids in feces samples from mice of a control group and mice on days 2 and 10 following induction of a kidney disorder.

FIG. 3(C) is a graph indicating fluctuations in the amounts of L-amino acids present in feces samples from mice of a control group (Sham) and mice on days 2 and 10 following induction of a kidney disorder. FIG. 3(D) is a graph indicating fluctuations in the ratio of D-amino acids/L-amino acids in feces sampled from mice of a control group and mice on days 2 and 10 following induction of a kidney disorder.

FIG. 3F indicates the results of evaluating for the presence of a statistically significant difference among the data shown in FIGS. 3(A) to 3(E). In the table, "<LOQ" indicates that the result is below the limit of quantification.

FIG. 11 is a table for investigating the relationship between estimated glomerular filtration rate (eGFR) and the amounts of each amino acid in feces in chronic kidney disease patients. A correlation coefficient of greater than 0.7 can be said to indicate a high correlation, a correlation coefficient of 0.4 to 0.7 can be said to indicate a correlation, and a correlation coefficient of 0.2 to 0.4 can be said to indicate a poor correlation.

MODES FOR CARRYING OUT THE INVENTION

Figure 1:
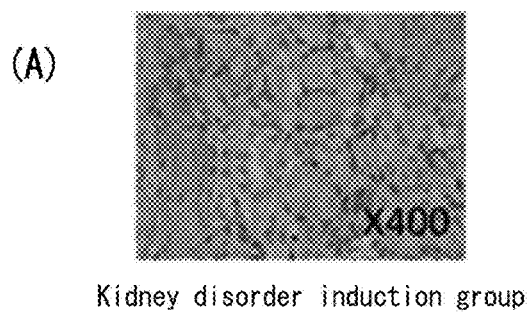
FIG. 1(A) is a micrograph showing staining of necrotic cells obtained by PAM staining of a kidney of a mouse of a kidney disorder induction group.
FIG. 1(B) is a graph obtained by measuring the percentage of necrotic cells in FIG. 1(A) in comparison with a control group.
Figure 1:
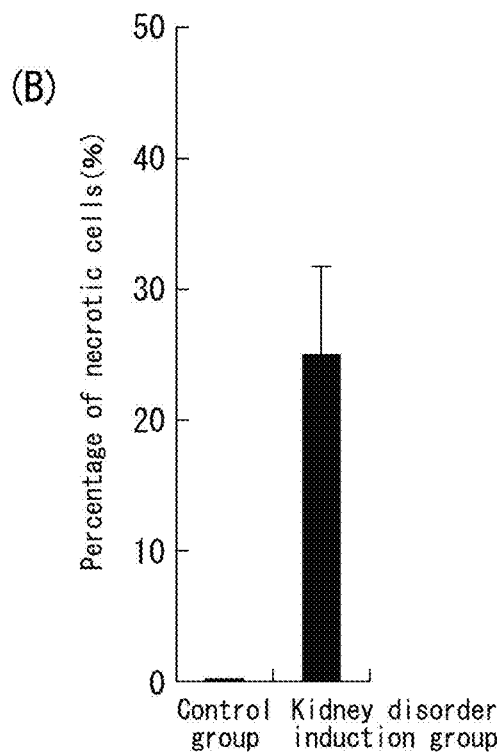

The method for analyzing feces or intestinal content according to the present invention comprises:

a step for measuring the amounts of the D-form and/or L-form of at least one amino acid, and a step for calculating a disease-state index value of a kidney disorder based on the amount of the D-form, the amount of the L-form, or the amount of the D-form and L-form, of the at least one type of amino acid.

This analytical method is able to provide data for diagnosis by a physician and can be said to be a preliminary diagnostic method. This analytical method may further comprise a step for correlating a disease-state index value of a kidney disorder with the pathology of a kidney disorder. This analytical method may be carried out by an analysis agency or analysis technician and results correlated with the pathology of a kidney disorder may be provided therefrom.

The sample analyzed in the present invention is feces or intestinal content. Thus, the sample may be excreted feces or impacted feces retained in the intestine. Intestinal content can be collected with an intestinal catheter, and intestinal flora may be collected directly in addition to feces. Feces collected by stool examinations are preferably used as sample from the viewpoints of convenience of collection and ease of testing. The collected sample may immediately be subjected to analysis after having dissolved or mixed in a solvent such as water, methanol, ethanol, acetonitrile, aqueous sodium borate solution or trifluoroacetic acid, or may be subjected to analysis after having stored at normal temperature or under refrigeration. After dissolving in a solvent, the sample may be submitted for analysis after subjecting to one round or a plurality of rounds of filtration and/or precipitation to remove insoluble matter. Measuring the weight of the feces or intestinal content used for the sample makes it possible to measure the amount of amino acid per unit sample weight. In addition, in cases in which the weight of the feces or intestinal content used for the sample cannot be measured, the sample can be dissolved in a solvent followed by diluting the sample by the further addition of solvent to make the amount of sample constant as determined on the basis of optical absorbance and the like. In the case of measuring after having made the amount of sample constant, the amount of amino acid in the present invention may be represented by weight or moles, or may be represented as a concentration.

In the present invention, the amino acids used as kidney failure markers are amino acids having enantiomers. More preferably, the amino acids are α-amino acids and even more preferably proteinogenic amino acids. Examples of such amino acids include alanine, cysteine, aspartic acid, glutamic acid, phenylalanine, histidine, isoleucine, lysine, leucine, methionine, asparagine, proline, glutamine, arginine, serine, threonine, valine, tryptophan and tyrosine. Here, since allo forms exist for isoleucine and threonine that have two asymmetric carbons, examples of enantiomers of L-isoleucine include D-isoleucine, D-allo-isoleucine and L-allo-isoleucine, and examples of enantiomers of L-threonine include D-threonine, D-allo-threonine and L-alto-threonine. In the present description, one or more forms selected from D-allo-form amino acids and L-allo-form amino acids in addition to D-form amino acids are used as the "D-form" for isoleucine and threonine. A disease-state index value of a kidney disorder can be calculated based on a measured value determined by measuring the amount of a D-form amino acid, amount of an L-form amino acid, or the combined amount of a D-form amino acid and L-form amino acid for at least one amino acid among these amino acids. One amino acid may be used alone or a plurality of amino acids, such as 2 to 19 amino acids, may be used in combination. From the viewpoint of obtaining a highly sensitive disease-state index value, it is preferable to use at least one amino acid selected from the group consisting of serine, arginine, aspartic acid, glutamic acid, alanine and proline, and more preferable to use at least one amino acid selected from the group consisting of serine, arginine and alanine. The aforementioned amino acids are amino acids that were selected using animal experimental models of early kidney disorder, and can also serve as markers of early kidney disorder in humans. In another aspect, at least one amino acid selected from the group consisting of histidine, asparagine, arginine, aspartic acid, allo-threonine, alanine, proline, methionine, valine, allo-isoleucine, isoleucine, leucine, phenylalanine, lysine and tyrosine is used preferably from the viewpoint of obtaining a highly sensitive disease-state index value for human kidney disorder, and particularly chronic kidney disease. From the viewpoint of obtaining a highly sensitive disease-state index value for human kidney disorder and particularly chronic kidney disease, histidine, asparagine, arginine, aspartic acid, allo-threonine, alanine, proline, valine, allo-isoleucine, leucine, phenylalanine or lysine is used more preferably, while histidine, allo-threonine or lysine is used most preferably. Serine, aspartic acid, glutamic acid, alanine, arginine, lysine or proline is used from the viewpoint of obtaining a disease-state index value for acute stage kidney disorder or kidney disorder caused by ischemia.

In one aspect of the present invention, at least one member selected from the group consisting of D+L-histidine, D+L-allo-threonine, D+L-asparagine, D+L-arginine, D+L-allo-isoleucine, D+L-phenylalanine, D+L-aspartic acid, D+L-methionine, D+L-valine, D+L-isoleucine, D+L-leucine, D+L-lysine, D+L-tyrosine, L-histidine, L-asparagine, L-arginine, L-phenylalanine, L-lysine, L-aspartic acid, L-alanine, L-methionine, L-valine, L-isoleucine, L-leucine, L-tyrosine, D-histidine, D-allo-threonine, D-lysine, D-allo-isoleucine, D-leucine, D-phenylalanine, D/L-histidine, D/L-lysine, D/L-aspartic acid, D/L-alanine, D/L-proline, D/L-valine and D/L-phenylalanine can be used as a disease-state index value from the viewpoint of the correlation with estimated glomerular filtration index (eGFR) ($|r|>0.2$). At least one member selected from the group consisting of D+L-histidine, D+L-allo-threonine, L-histidine, D-histidine, D-allo-threonine, D-lysine, D/L-histidine, D/L-lysine, D+L-asparagine, D+L-arginine, D+L-allo-isoleucine, D+L-phenylalanine, L-asparagine, L-arginine, L-phenylalanine, L-lysine, D-allo-isoleucine, D-leucine, D-phenylalanine, D/L-aspartic acid, D/L-alanine, D/L-proline, D/L-valine and D/L-phenylalanine is more preferably used as a disease-state index value from the viewpoint of a higher correlation with eGFR ($|r|>0.4$). At least one member selected from the group consisting of D+L-histidine, D+L-allo-threonine, L-histidine, D-histidine, D-allo-threonine, D-lysine, D/L-histidine and D/L-lysine is even more preferably used from the viewpoint of an even higher correlation with eGFR ($|r|>0.7$). Furthermore, in the present invention, the term D+L-amino acid refers to the total of the D-form and the L-form of that amino acid, while the term D/L-amino acid refers to the ratio of the D-form to the L-form of that amino acid.

Measurement of the amount of a D-amino acid in a sample in the present invention may be carried out using any method commonly known among persons with ordinary skill in the art. For example, a method consisting of preliminarily stereospecifically derivatizing a D-amino acid and L-amino acid with o-phthalaldehyde (OPA), N-tert-butyloxycarbonyl-L-cysteine (Boc-L-Cys) or other modifying reagent, followed by separating the enantiomers by subjecting a mixture thereof with 100 mM acetate buffer (pH 6.0) and acetonitrile to gradient elution using an analytical column in the manner of ODS-80TsQA can be used to simultaneously measure the D-form and L-form of an amino acid. In addition, a method consisting of preliminarily derivatizing a D-amino acid and L-amino acid with a fluorescent reagent in the manner of 4-fluoro-7-nitro-2,1,3-benzoxadiazole (NBD-F), followed by non-stereospecifically separating each amino acid using an analytical column in the manner of ODS-80TsQA or Mightysil RP-18GP and subsequently optically resolving the amino acids using a Pirkle-type chiral stationary phase column (such as Sumichiral OA-2500S or R) can be used to measure trace amounts of proteinogenic amino acids (Yokose, K. and K. Zaitsu, Analytical Chemistry, Vol. 53, 677-690 (2004)). An optical resolution column system in the present description refers to a separation analysis system that at least uses an optical resolution column, and may include separation analysis by an analytical column other than an optical resolution column. More specifically, the concentrations of D-form and L-form amino acids in a sample can be measured by using an optical isomer analytical method comprising a step for passing a sample containing a component having optical isomers through a first liquid serving as a mobile phase and a first column packing serving as a stationary phase to separate the aforementioned components in the aforementioned sample, a step for separately retaining each of the components in the sample in multi-loop units, a step for supplying each component in the sample separately retained in the multi-loop units to a second liquid serving as a mobile phase and a second column packing having an optically active center serving as a stationary phase by passing through a flow path thereof to separate the aforementioned optical isomers respectively contained in each component of the sample, and a step for detecting the optical isomers respectively contained in each component of the sample (Japanese Patent No. 4291628). Alternatively, D-amino acids can be quantified by an immunological technique using monoclonal antibody that identifies an optical isomer of an amino acid, such as monoclonal antibody that specifically binds with an amino acid such as D-leucine or D-aspartic acid (Japanese Patent Application No. 2008-27650).

In the present invention, a kidney disorder refers to all disease/injuries occurring in the kidneys, and includes not only kidney failure, but also changes leading to kidney failure. Kidney failure refers to a state in which kidney function has decreased to a level below normal kidney function, and includes all kidney disorder used in the normal sense of the word. Although there are no limitations thereon, kidney failure generally refers to a state in which kidney function has fallen below 30% of normal kidney function, and is classified as acute kidney injury or chronic kidney disease. There are multiple causes of decreased kidney function, examples of which include immune system abnormalities or drug allergies, hypertension, diabetes, hemorrhage or sudden drops in blood pressure, infections and dehydration associated with burns. Classifications of acute kidney injury have been advocated that classify according to disease stage in the manner of the RIFLE, AKIN and KDIGO classifications, classify acute kidney injury into categories consisting of Risk (Stage 1), Injury (Stage 2) and Failure (Stage 3), and further classify as Loss and End Stage Kidney Disease corresponding to the duration thereof. All of these classifications use serum creatinine level and urine volume as indices, and for example, evaluation criteria consist of a rise in serum creatinine level 1.5 to 2.0 times the baseline or urine volume of less than 0.5 ml/kg for 6 hours or more for the Risk (Stage 1) classification, a rise in serum creatinine level 2.0 to 3.0 times the baseline or urine volume of less than 0.5 ml/kg for 12 hours or more for the Injury (Stage 2) classification, and a rise in serum creatinine level greater than 3.0 times the baseline or urine volume of less than 0.3 ml/kg for 24 hours or more for the Failure (Stage 3) classification. On the other hand, these classifications are able to categorize acute kidney injury more accurately by combining with the use of other indices such as the amount of change in GFR. The 2009 guidelines of the Japanese Society of Nephrology indicate evaluation criteria for chronic kidney disease (CKD) ranging from disease stage 1 (kidney disorder with normal kidney function, eGFR≥90) to disease stage 5 (kidney failure, eGFR<15). Estimated glomerular filtration rate (eGFR), serving as the index, is calculated on the basis of serum creatinine level, age and gender, and indicates the ability of the kidneys to excrete waste products in urine. According to the analytical and testing methods of the present invention, decreases in kidney function can be detected with higher sensitivity than previous kidney function markers. Thus, kidney failure can be classified into kidney disorder risk groups at an earlier stage for which classification of kidney failure was not possible with conventional markers, thereby enabling, for example, decreases in kidney function to be detected even in risk groups in which, although there are risk factors for AKI or CKD in the manner of the aforementioned causes, there are no well-defined fluctuations in serum creatinine or eGFR observed. In particular, amino acids selected using experimental animal models of early kidney disorder can serve as markers for kidney disorder at an earlier stage in humans.

Calculation of the disease-state index value for a kidney disorder in the present invention is carried out based on the amounts of the D-form and/or L-form of an amino acid. In addition, in a different aspect, the disease-state index value is calculated based on the total amount of the D-form and L-form of an amino acid.

In the present description, a disease-state index value may refer to the amount of an individual biomarker or a calculable numerical value based on the amounts of a plurality of biomarkers. The disease-state index value used in the present description may be the amount of the D-form of a certain amino acid, the amount of the L-form of a certain amino acid, the ratio of the amount of the D-form of a certain amino acid to a enantiomer thereof, such as the ratio of the amount of the D-form of a certain amino acid to the amount of the L-form thereof or the ratio of the amount of the L-form of a certain amino acid to the amount of the D-form thereof, or the ratio of the amount of the D-form of a certain amino acid to the sum of the amounts of the D-form and L-form thereof. In the case of using the ratio of the amounts of enantiomers of a certain amino acid as a disease-state index value, there is the advantage of eliminating the need for corrections for the amount and volume of the sample. In calculating a disease-state index value, an arbitrary variable capable of having an effect on the amount of a chiral amino acid, such as an arbitrary constant, age, body weight, gender, BMI or eGFR, may be added, subtracted, multiplied or divided provided it is used as a diagnostic marker for kidney disorder.

In the analytical method and testing method of the present invention, a correlation can be made between the disease-state index value of a subject and the pathology of a kidney disorder based on a disease-state index reference value determined based on disease-state index values preliminarily measured in a healthy subject group and kidney disorder patient group. The disease-state index reference value may also be a threshold value. A person with ordinary skill in the art would be able to suitably set a threshold value based on the disease-state index values of a healthy subject group and kidney failure patient group. Examples of values able to be used as a threshold value include, but are not limited to, the average value, median value or X percentile value of a healthy subject group or kidney failure patient group. Here, an arbitrary value can be selected for X, and a value of 3, 5, 10, 15, 20, 30, 40, 60, 70, 80, 85, 90, 95 or 97 can be used suitably. A single threshold value can be set or a plurality of threshold values can be set corresponding to the type (acute or chronic) or cause (such as drug-induced nephropathy, diabetic nephropathy, IgA nephropathy, membranous nephropathy or nephrosclerosis) of the kidney failure, stage (such as early, intermediate or late) and the amino acids or combination thereof used, while pathology can be classified corresponding to severity. The pathology of kidney failure of a subject can be evaluated, determined or diagnosed by comparing a previously set threshold value with the disease-state index value of the subject. In still another aspect, a threshold value (cutoff value) can also be determined by carrying out ROC analyses between a healthy subject group and patient groups at each stage of a kidney disorder.

In another aspect of the present invention, the present invention relates to a method for testing for a kidney disorder by using feces or intestinal content as sample. This testing method includes the steps indicated below:

a step for measuring the amounts of the D-form and/or L-form of at least one proteinogenic amino acid, and a step for calculating a disease-state index value of a kidney disorder based on the amount of the D-form, the amount of the L-form, or the amount of the D-form and L-form, of the at least one type of amino acid, and further includes:

a step for correlating the disease-state index value of the kidney disorder with the pathology of the kidney disorder.

This testing method may be carried out by an analysis agency or analysis technician and results correlated with the pathology of a kidney disorder may be provided therefrom. Reagents used in this testing method, pathology of a correlating kidney disorder and each of the steps carried out may be the same as those defined in the aforementioned analytical method.

Figure 8:
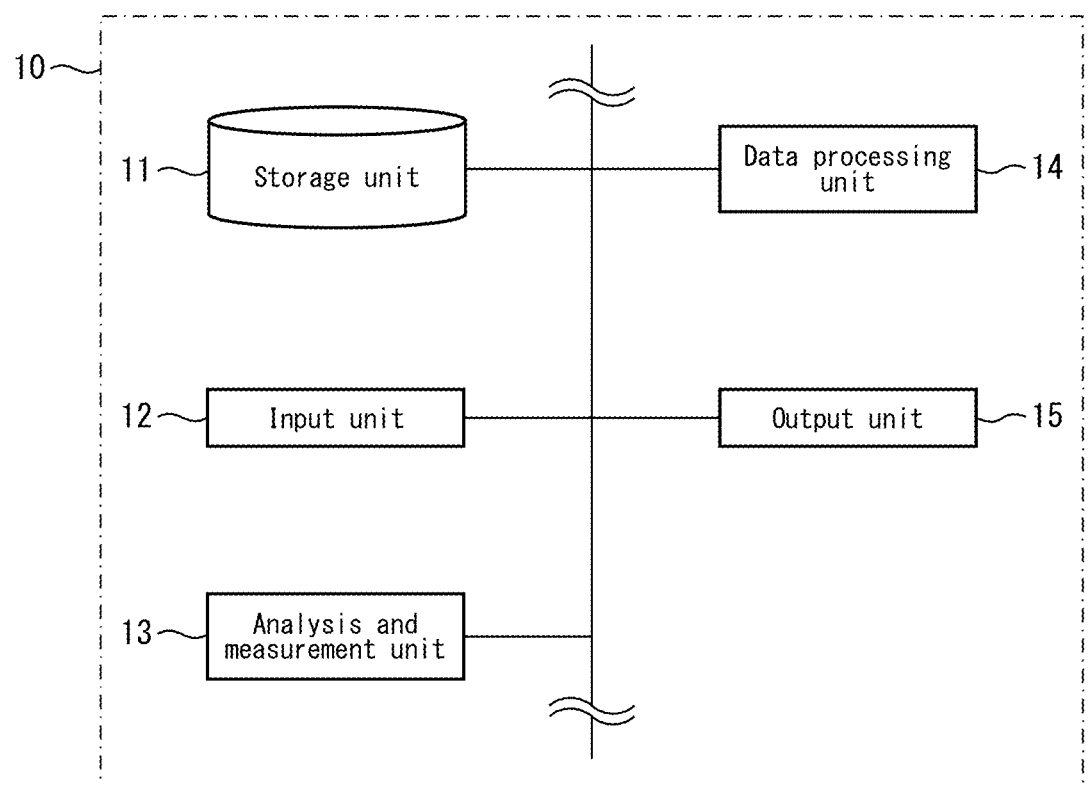
FIG. 8 is a block diagram of the sample analysis system of the present invention.

FIG. 8 is a block diagram of the sample analysis system of the present invention. A sample analysis system 10 of the present invention shown in FIG. 8 is configured so as to be able to carry out the analytical method and testing method of the present invention. This sample analysis system 10 comprises a storage unit 11, an input unit 12, an analysis and measurement unit 13, a data processing unit 14 and an output unit 15, and is able to output pathological information by analyzing a sample of feces or intestinal content. More specifically, in the sample analysis system 10 of the present invention:

the storage unit 11 stores threshold values of disease-state index values for identifying kidney disorder input from the input unit 12, the analysis and measurement unit 13 separates and quantifies amino acid enantiomers of at least one proteinogenic amino acid present in the feces or intestinal content of the subject, the data processing unit 14 calculates a disease-state index value of a kidney disorder based on the amount of the D-form, the amount of the L-form or the amount of the D-form and L-form of the at least one amino acid, the data processing unit 14 identifies pathological information of a kidney disorder by comparing with threshold values stored in the storage unit 11, and the output unit 15 outputs pathological information on the kidney disorder of the subject.

The storage unit 11 has, for example, a memory device such as RAM, ROM or flash memory, a hard disk device such as a hard disk drive, or a portable storage device such as a flexible disk or optical disk. The storage unit stores data measured with the analysis and measurement unit, data and instructions entered from the input unit, arithmetic processing results made with the data processing unit, as well as a computer program or database used for various types of processing by an information processing device. The computer program may be installed with a computer-readable storage medium such as a CD-ROM or DVD-ROM or may be installed via the Internet. The computer program is installed in the storage unit using a known setup program.

The input unit 12 is an interface and the like, and comprises an operating unit such as a keyboard or mouse. As a result, the input unit allows, for example, input of data measured with the analysis and measurement unit 13 or arithmetic processing instructions made with the data processing unit 14. In addition, the input unit 12 may also comprise an interface separate from the operating unit that enables input of measured data and the like via a network or storage medium in the case, for example, the analysis and measurement unit is located externally.

The analysis and measurement unit 13 carries out the step for measuring amounts of the D-form and L-form of an amino acid in a sample of feces or intestinal content suspended in a solvent. Thus, the analysis and measurement unit 13 has a configuration that enables separation and measurement of the D-form and L-form of an amino acid. Although amino acids may be analyzed one at a time, some or all types of amino acids can be analyzed collectively. Without intending to be limited thereto, the analysis and measurement unit 13 may be, for example, a high-performance chromatography system equipped with a sample introduction unit, optical resolution column and detection unit. The analysis and measurement unit 13 may also be configured separately from the sample analysis system, and data such as measured data may be input via the input unit 12 using a network or storage medium.

The data processing unit 14 is configured so as to identify a kidney disorder by calculating the disease-state index value of a kidney disorder based on the amounts of the D-form or D-form and L-form of each amino acid measured, and comparing with threshold values stored in the storage unit 11. The data processing unit 14 executes various types of arithmetic processing in accordance with a program stored in the storage unit 11. Arithmetic processing is carried out by a CPU contained in the data processing unit. This CPU is able to carry out various types of control by containing a function module that controls the analysis and measurement unit 13, input unit 12, storage unit 11 and output unit 15. Each of these units may be configured with respectively independent components such as integrated circuits, microprocessors or firmware.

The output unit 15 is configured so as to output the results of arithmetic processing from the data processing unit in the form of disease-state index values and/or pathological information. The output unit 15 may be an output means such as a printer or a liquid crystal display or other type of display device that directly displays the results of arithmetic processing, or may be an interface unit for outputting results to an external storage device or via the Internet.

Figure 9A:
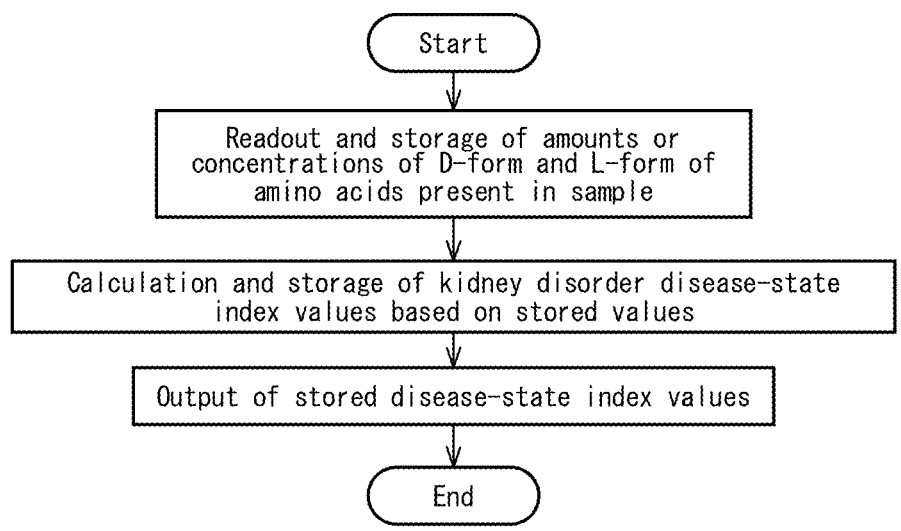
FIGS. 9(A) and 9(B) are flow charts showing examples of operations for determining a disease-state index value.
Figure 9B:
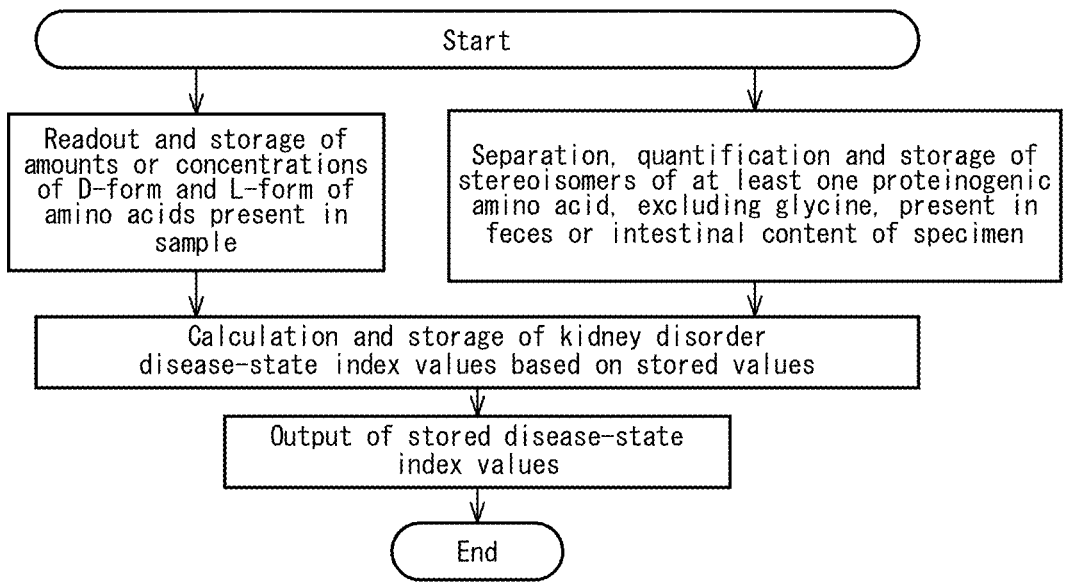
Figure 9C:
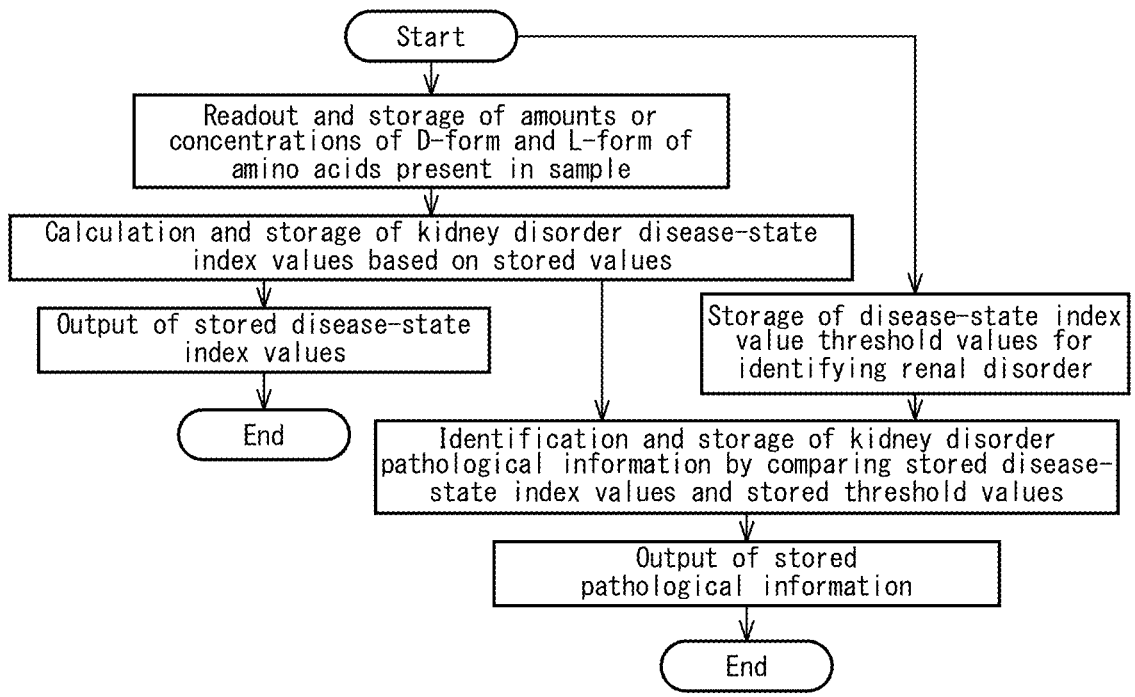
FIGS. 9(C) and 9(D) are flow charts showing examples of operations for determining a disease-state index value and/or pathological information.
Figure 9D:
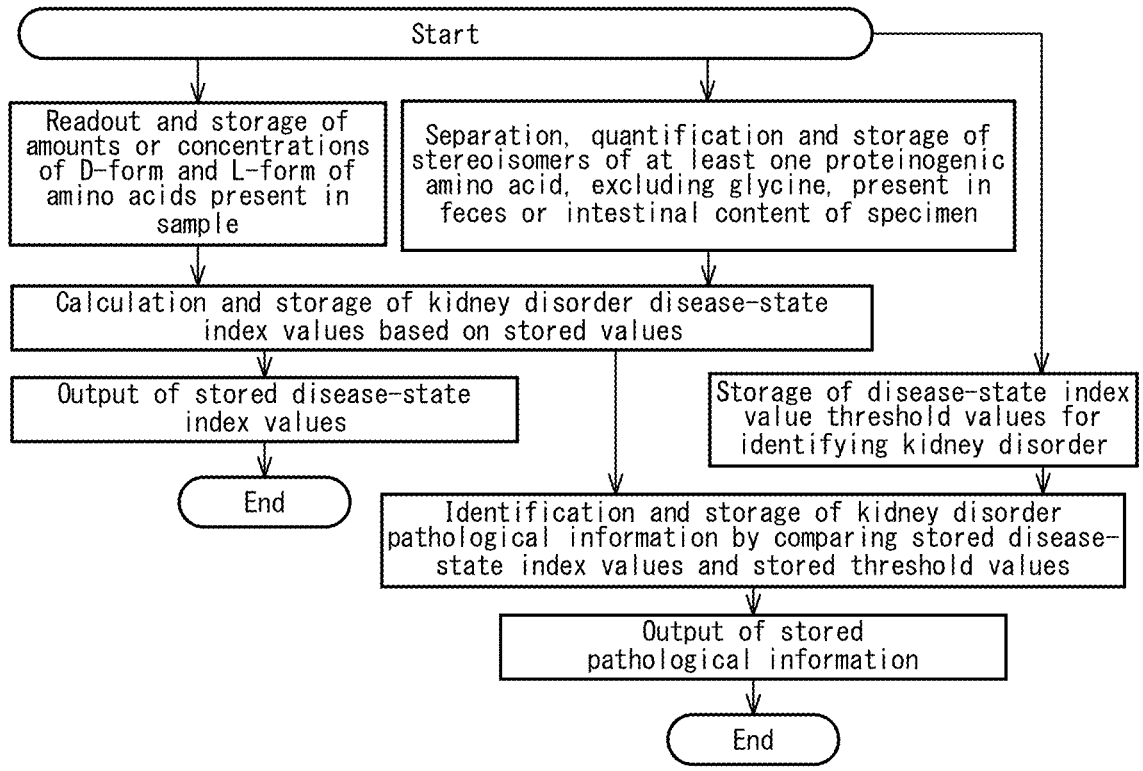
Figure 10A:
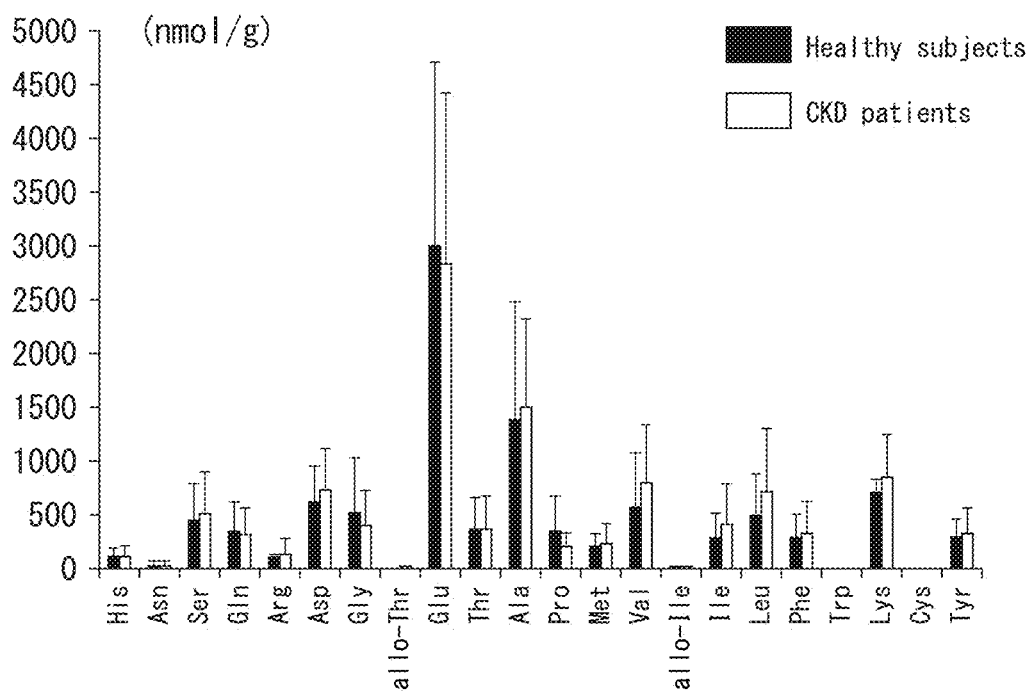
FIG. 10(A) is a graph indicating the amounts of D-amino acids and L-amino acids (total amino acids) in feces sampled from healthy subjects and chronic kidney disease patients.
Figure 10B:
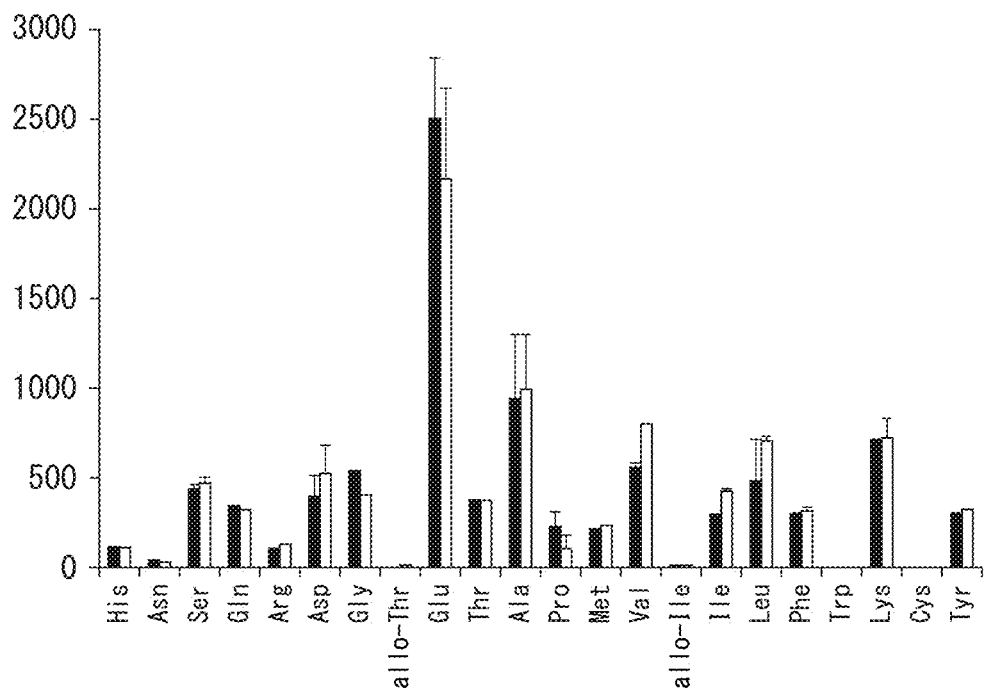
FIG. 10(B) is a graph indicating the amounts of L-amino acids in feces sampled from healthy subjects and chronic kidney disease patients.
Figure 10:
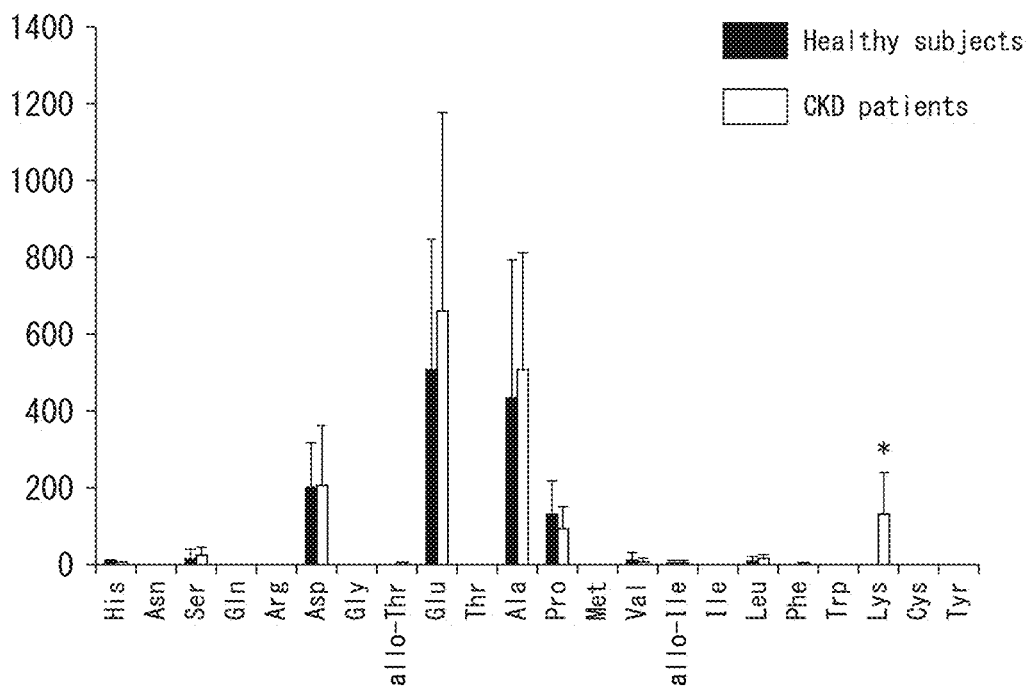
FIG. 10(C) is a graph indicating the amounts of D-amino acids in feces sampled from healthy subjects and chronic kidney disease patients.
FIG. 10(D) is a graph indicating the ratios of D-amino acid/L-amino acid in feces sampled from healthy subjects and chronic kidney disease patients.
Figure 10:
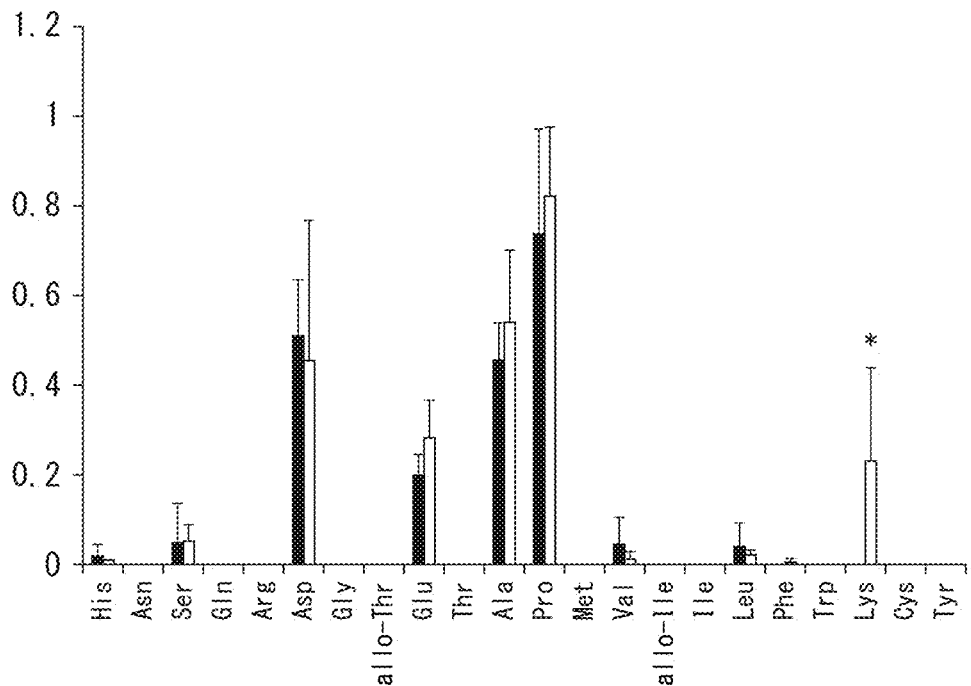
Figure 12:
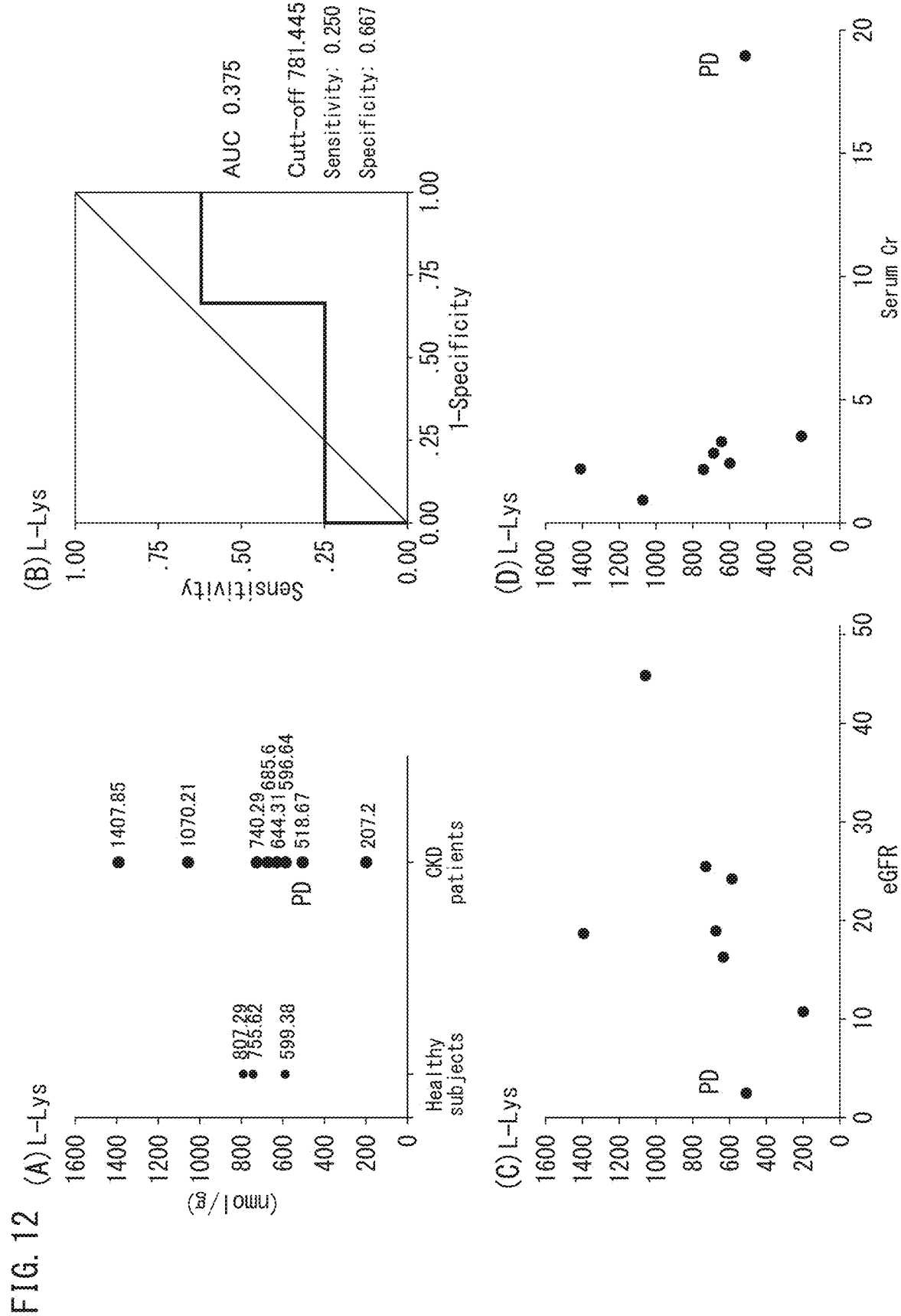
FIG. 12 depicts (A) a graph showing the amounts of L-Lys in chronic kidney disease patients and healthy subjects, (B) a graph indicating ROC curves for chronic kidney disease patients and healthy subjects, (C) a scatter diagram of estimated glomerular filtration rate (eGFR) versus L-Lys levels in chronic kidney disease patients, and (D) a scatter diagram of serum creatinine levels versus L-Lys levels in chronic kidney disease patients.
Figure 13:
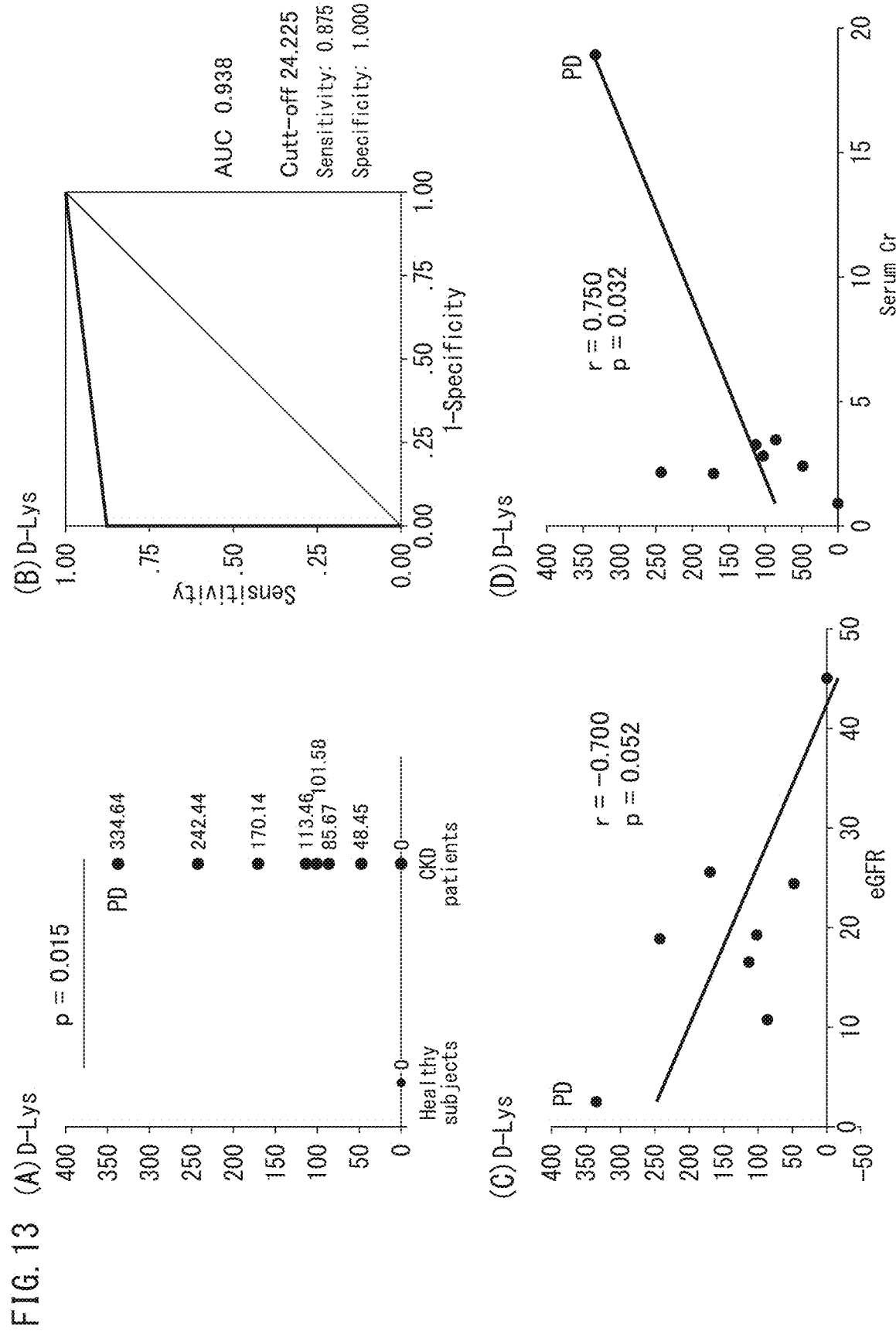
FIG. 13 depicts (A) a graph showing the amounts of D-Lys in chronic kidney disease patients and healthy subjects, (B) a graph indicating ROC curves for chronic kidney disease patients and healthy subjects, (C) a scatter diagram of estimated glomerular filtration rate (eGFR) versus D-Lys levels in chronic kidney disease patients, and (D) a scatter diagram of serum creatinine levels versus D-Lys levels in chronic kidney disease patients.
Figure 14:
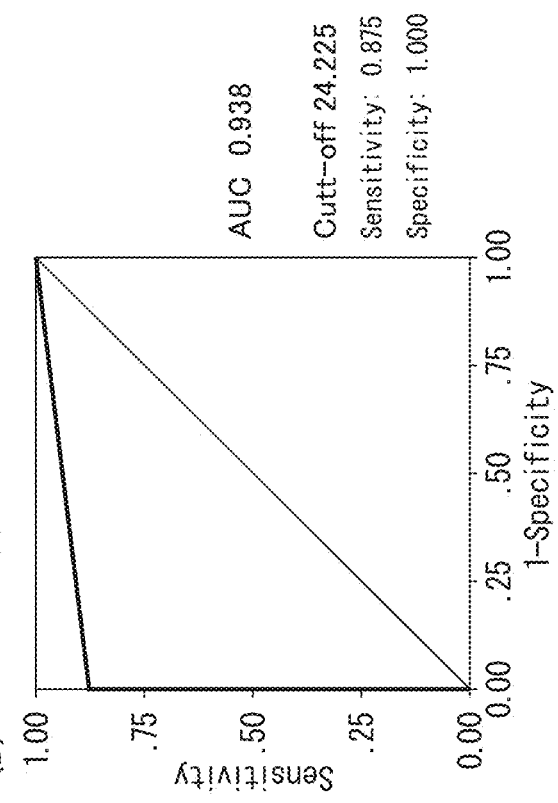
FIG. 14 depicts (A) a graph showing D-Lys/L-Lys ratios in chronic kidney disease patients and healthy subjects, (B) a graph indicating ROC curves for chronic kidney disease patients and healthy subjects, (C) a scatter diagram of estimated glomerular filtration rate (eGFR) versus D-Lys/L-Lys ratios in chronic kidney disease patients, and (D) a scatter diagram of serum creatinine levels versus D-Lys/L-Lys ratios in chronic kidney disease patients.
Figure 14:
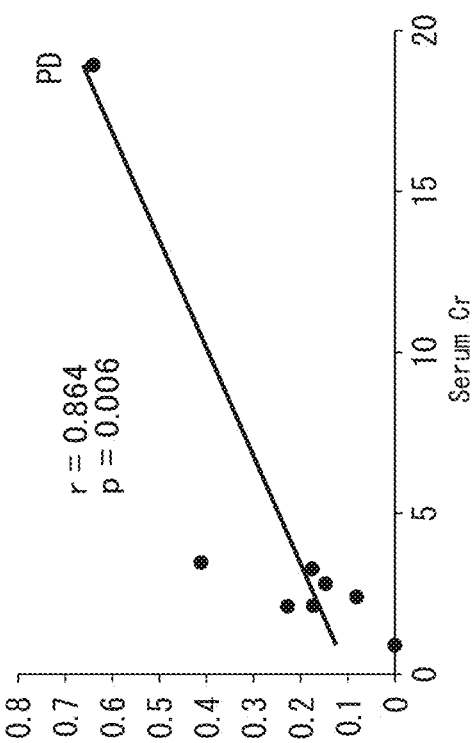
Figure 14:
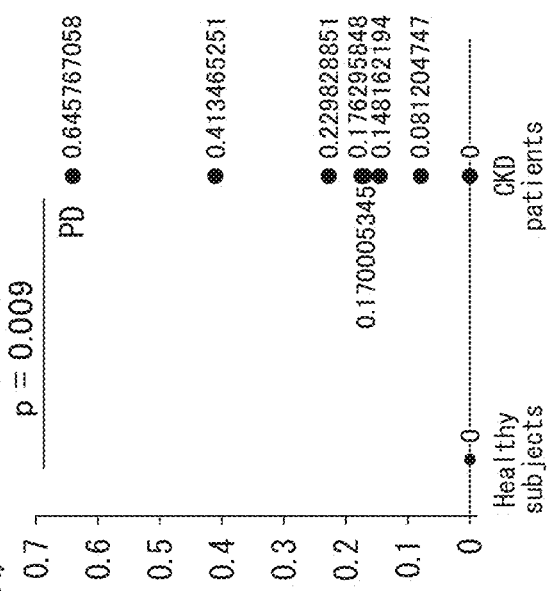
Figure 14:
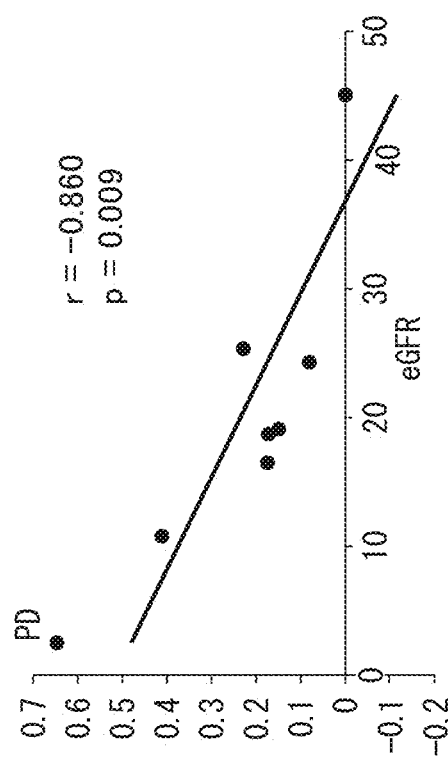

FIGS. 9(A) and 9(B) are flow charts indicating examples of operations for determining a disease-state index value with the program of the present invention. FIGS. 9(C) and 9(D) are flow charts indicating examples of operations for determining disease-state index values and pathological information with the program of the present invention.

More specifically, the program of the present invention is a program for allowing an information processing device, comprising an input unit, output unit, data processing unit and storage unit, to determine disease-state index values and/or pathological information. The program contains instructions for allowing the aforementioned information processing device to execute the following operations:

storage of the amounts of the D-form, L-form or D-form and L-form of at least one amino acid input from the input unit by the storage unit, calculation of a disease-state index value by the data processing unit based on values stored in the storage unit, storage of the calculated disease-state index value by the storage unit, and output of the stored pathological information by the output unit.

The program of the present invention may be contained in a storage medium or may be provided via a telecommunication line such as the Internet or LAN.

In the case the information processing device is provided with an analysis and measurement unit, instead of inputting values for the amount of the D-form, amount of the L-form or amount of the D-form and L-form of at least one amino acid from the input unit, the analysis and measurement unit may contain commands for allowing the information processing device to measure those values from a feces sample and store in the storage unit.

In order to determine pathological information, the analysis and measurement unit may further contain commands for allowing the information processing device to execute identification of the pathology of a kidney disorder by having the data processing unit compare stored disease-state index values and threshold values preliminarily stored in the storage unit, storage of the identified pathological information in the storage unit, and output of the stored pathological information to the output unit.

In the present invention, the subject is not limited to a human, but rather can also include experimental animals such as mice, rats, rabbits, dogs or monkeys. Thus, a subject may also be referred to as a specimen.

The analytical method of the present invention can be used to gather preliminary data for a method for diagnosing chronic kidney disease and/or acute kidney injury. Although a physician is able to diagnose chronic kidney disease and/or acute kidney injury by using this preliminary data, this analytical method may also be carried out by a non-physician such as a medical assistant, or can be carried out by a facility such as an analysis agency. Thus, the analytical method of the present invention can also be said to be a preliminary diagnostic method.

A treatment plan can also be determined by referring to the results of the analytical method and testing method of the present invention. Although not limited to the following, in the case of identifying to be a chronic kidney disease, it is necessary to additionally provide treatment such as improvement of lifestyle, dietary guidance, blood pressure management, blood glucose level management or lipid management. Examples of recommended lifestyle improvements include quitting smoking and exercise for lowering BMI. Examples of recommended dietary guidance include reduced salt intake for the purpose of improving hypertension. Examples of recommended blood pressure management include administration of ACE inhibitors and ARB for the purpose of improving hypertension. Examples of recommended blood sugar level management include administration of insulin for the purpose of lowering HbA1c. Examples of recommended lipid management include administration of hyperlipidemia drugs for the purpose of lowering LDL cholesterol. These treatment plans are determined based on chiral amino acid levels after having consulted with a physician. Thus, in another aspect thereof, the present invention relates to a method for treating a kidney disorder comprising carrying out the analytical method and testing method of the present invention followed by further providing treatment for the kidney disorder.

All documents mentioned in the present description are incorporated in the present description in their entirety by reference.

Examples of the present invention explained below are provided for the purpose of exemplification only, and are not intended to limit the technical scope of the present invention. The technical scope of the present invention is only limited by the description of the claims. The present invention can be altered, such as by addition, deletion or substitution of constituents of the present invention, on the condition that such alteration does not deviate from the gist of the present invention.

EXAMPLES

Example 1

Materials and Methods

Research Ethics

All experiments were conducted in accordance with facility guidelines and were approved by the animal care and use committee of that facility.

Materials

Amino acid enantiomers and HPLC-grade acetonitrile were purchased from Nacalai Tesque (Kyoto). HPLC-grade methanol, trifluoroacetic acid and boric acid were purchased from Wako Pure Chemical Industries (Osaka). Water was purified using the Milli-Q Gradient A10 System.

Production of Animal Model of Mild Acute Kidney Injury by Clipping Kidney Artery and Kidney Vein The skin and peritoneum of six-week-old C57BL/6JJic male mice (Clea Japan) were incised under anesthesia. The kidney artery and kidney vein were clipped for 40 minutes and warmed with a heating plate at 37° C. during that time. The clips were then released and the peritoneum and skin were sutured. An ischemic kidney disorder was inducted by clipping the kidney artery and vein. A kidney disorder induction group used for induction of ischemic kidney disorder and a control group that had only undergone a sham procedure were used in the experiments.

Evaluation of Tissue Sections for Ischemic Kidney Disorder

Figure 2:
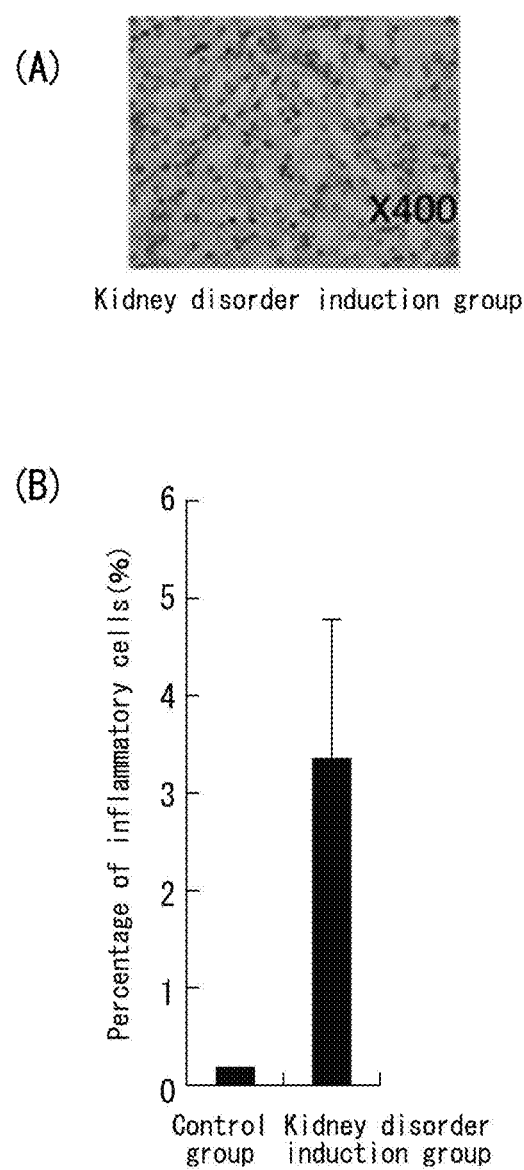
FIG. 2(A) is a micrograph showing staining of inflammatory cells (macrophages and monocytes) obtained by F4/80 staining of a kidney of a mouse of a kidney disorder induction group.
FIG. 2(B) is a graph obtained by measuring the percentage of inflammatory cells in FIG. 2(B) in comparison with a control group.

The mice were sacrificed on day 2 following induction of ischemic kidney disorder followed by recovery of kidney tissue. Fixation treatment was carried out on the recovered kidney tissue. Sections were acquired from the fixed kidney tissue followed by PAS staining. F4/80 staining was carried out on other sections. The result of PAS staining is shown in FIG. 1(A). The percentage of necrotic cells was evaluated based on the staining result of FIG. 1(A). Those results are shown in the graph of FIG. 1(B). The result of F4/80 staining is shown in FIG. 2(A). The percentage of necrotic cells was evaluated based on the staining result of FIG. 2(A). Those results are shown in the graph of FIG. 2(B).

Evaluation Using Markers for Ischemic Kidney Disorder

Blood and urine samples were collected from the mice on day 2 following induction of ischemic kidney disorder. The collected blood samples were centrifuged for 10 minutes at 1500×g in Becton Dickinson Microtainer blood collection tubes to separate the serum. Serum creatinine was measured using the Fuji DRI-CHEM 4000 System (FujiFilm, Tokyo). Next, KIM-1 and NGAL levels in urine were quantified using the Mouse ELISA Kit manufactured by R&D Systems.

Based on these results, clipping of the kidney artery and kidney vein carried out in the present example was indicated to induce a kidney disorder to a degree that was unable to be detected by conventional kidney failure markers.

Analysis of Amino Acids Present in Feces Samples in a Mild Ischemic Kidney Disorder Disease Animal Model Feces collected from the large intestines of mice of a control group (sham) and kidney disorder induction group on day 2 and day 10 following induction of ischemic kidney disorder were dissolved in methanol and introduced into an amino acid enantiomer analysis system according to the D-,L-amine acid simultaneous high sensitivity analysis system developed by Zaitsu, et al (Japanese Patent No. 4291628). Details regarding the analysis conditions for each amino acid are explained in Miyoshi, Y. et al, J. Chromatogr. B, 879: 3184 (2001) and Sasabe, J. et al, Proc. Natl. Acad. Sci. U.S.A., 109: 627 (2012). Briefly speaking, amino acids present in feces were derivatized with 4-fluoro-7-nitro-2,1,3-benzoxadiazole (NBD-F, Tokyo Chemical Industry Co.) and then introduced into an HPLC system (Nanospace SI-2, Shiseido, refer to supplementary information). Briefly speaking, an in-house monolithic ODS column (inner diameter: 0.53 mm×500 mm) was used for the reversed phase separation analytical column. Fluorescence was detected at an excitation wavelength of 470 nm and detection wavelength of 530 nm. Following reversed phase separation, the amino acids were transferred to an optical resolution column. The Sumichiral OA-2500S column (1.5 mm×250 mm, self-packing, packing manufactured by Sumika Chemical Analysis Service Ltd.) using (S)-napthylglycine as chiral selector was used for enantiomer separation. The total amount of amino acid, amount of D-amino acid, amount of L-amino acid, ratio of D-amino acid/L-amino acid and ratio of D-amino acid/(D+L) amino acid are respectively shown in FIGS. 3(A) to 3(E) for each amino acid.

Statistical Processing

All values described in the present description and drawings are indicated as the mean±standard error of the mean (SEM). Statistical techniques used for statistical analysis of the experiments included the two-sided Student's t-test, one-way analysis of variance (ANOVA) and Tukey's multiple comparison test. In addition, a result was evaluated as being significant when the P value obtained in these tests was less than 0.05. Prism 5 (GraphPad Software, La Hoya, Calif.) was used for all analyses.

Results

Changes in Amounts of D-Amino Acids

The results of analyzing changes in the amounts of D-amino acids in feces are shown in FIG. 3(B). Significant changes in the amounts of D-amino acids in the kidney disorder induction group in comparison with the control group (sham) were observed for serine, aspartic acid, glutamic acid, alanine and proline. Among these, the amounts of serine and proline were higher in comparison with the control group (sham) on both post-procedure days 2 and 10, and were higher on day 10 than on day 2. Although the amounts of aspartic acid and alanine decreased in comparison with the control group (sham) on post-procedure day 2, the amounts thereof were higher than the control group on day 10. Although there were no changes observed in the amount of glutamic acid on day 2, the amount increased on day 10. Although the patterns of these changes were not constant, differences in the amounts of serine, aspartic acid, alanine and proline appeared on day 2 of the fastigium period of the kidney disorder, indicating that these amino acids are able to function as detection markers for mild kidney disorder. Upon conducting more detailed analyses, since the D-forms of serine and proline increased on day 2, these D-amino acids are able to identify mild kidney disorder in the case the amounts thereof in feces and intestinal content are higher than a threshold value. In addition, since the D-forms of aspartic acid and alanine decreased on day 2 of the fastigium period of the kidney disorder, these D-amino acids are able to identify mild kidney disease/ injuries in the case the amounts thereof in feces and intestinal content are lower than a threshold value. However, there is the possibility of a change in the presence or absence of a significant difference caused by increasing the parameters, and in that case, since these amino acids can be used to detect mild kidney disorder in the present invention, the amino acids are not necessarily limited to those exemplified above.

Changes in Ratio of D-Amino Acid/L-Amino Acid

The results of analyzing changes in the ratio of the amount of D-amino acids to the amount of L-amino acids (D-amino acid/L-amino acid) in feces are shown in FIG. 3(D). Significant changes in the ratio of the amount of D-amino acid/L-amino acid in the kidney disease/injury induction group in comparison with the control group (sham) were observed for serine, arginine and aspartic acid. Among these, the ratios for serine and arginine were higher in comparison with the control group (sham) on both post-procedure days 2 and 10, and were higher on day 10 than on day 2. On the other hand, in the case of aspartic acid, the ratio was lower in comparison with the control group (sham) on both post-procedure days 2 and 10 and there was hardly any difference observed between days 2 and 10. Upon conducting more detailed analyses, since the ratio of the D-form/L-form increased on day 2 for serine and arginine, the ratio of the D-form/L-form of these amino acids present in feces or intestinal content can be used to identify mild kidney disorder in the case of being higher than a threshold value. In addition, in the case of aspartic acid, since the ratio decreased on day 2 of the fastigium period of the kidney disorder, this D-amino acid present in feces or intestinal content can be used to identify mild kidney disorder in the case of being lower than a threshold value. However, there is the possibility of a change in the presence or absence of a significant difference by increasing the parameters, and in that case, since these amino acids can be used to detect mild kidney disorder in the present invention, the amino acids are not necessarily limited to those exemplified above. In the case of the ratio of the D-form/L-form in particular, although there were no significant differences observed, since histidine, glutamine, glutamic acid, valine and leucine exhibited behavior different from that of the control on day 2 of the fastigium period of the kidney disorder, they have the potential to be useful for diagnosing mild kidney disorder.

Changes in Ratio of D-Amino Acid/(D-Amino Acid+L-Amino Acid)

Figure 3E:
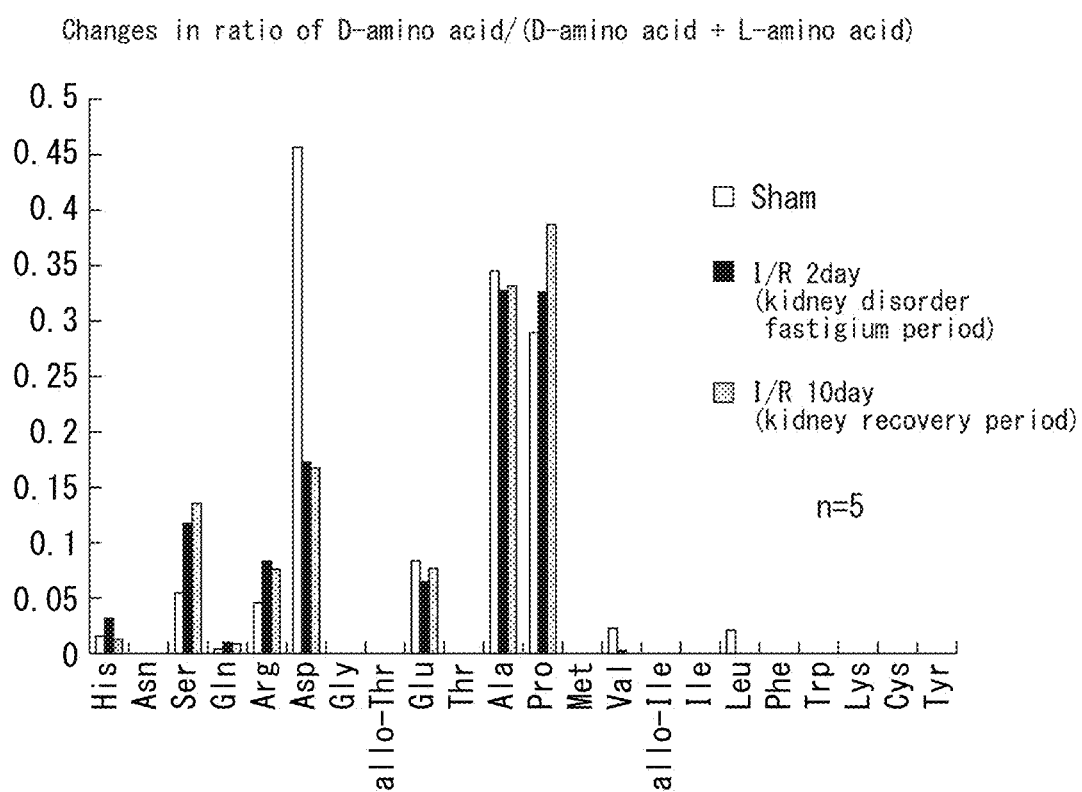
FIG. 3(E) is a graph indicating fluctuations in the ratio of D-amino acids/(D-amino acids+L-amino acids) in feces samples from mice of a control group (Sham) and mice on days 2 and 10 following induction of a kidney disorder.

The results of analyzing changes in the ratio of D-amino acid to the total amount of D-amino acid and L-amino acid (D-amino acid/D-amino acid+L-amino acid) in feces are shown in FIG. 3(E). In addition, the data shown in FIGS. 3(A) to 3(E) was evaluated for the presence of a statistically significant difference. Those results are shown in FIG. 3F.

Figure 4:
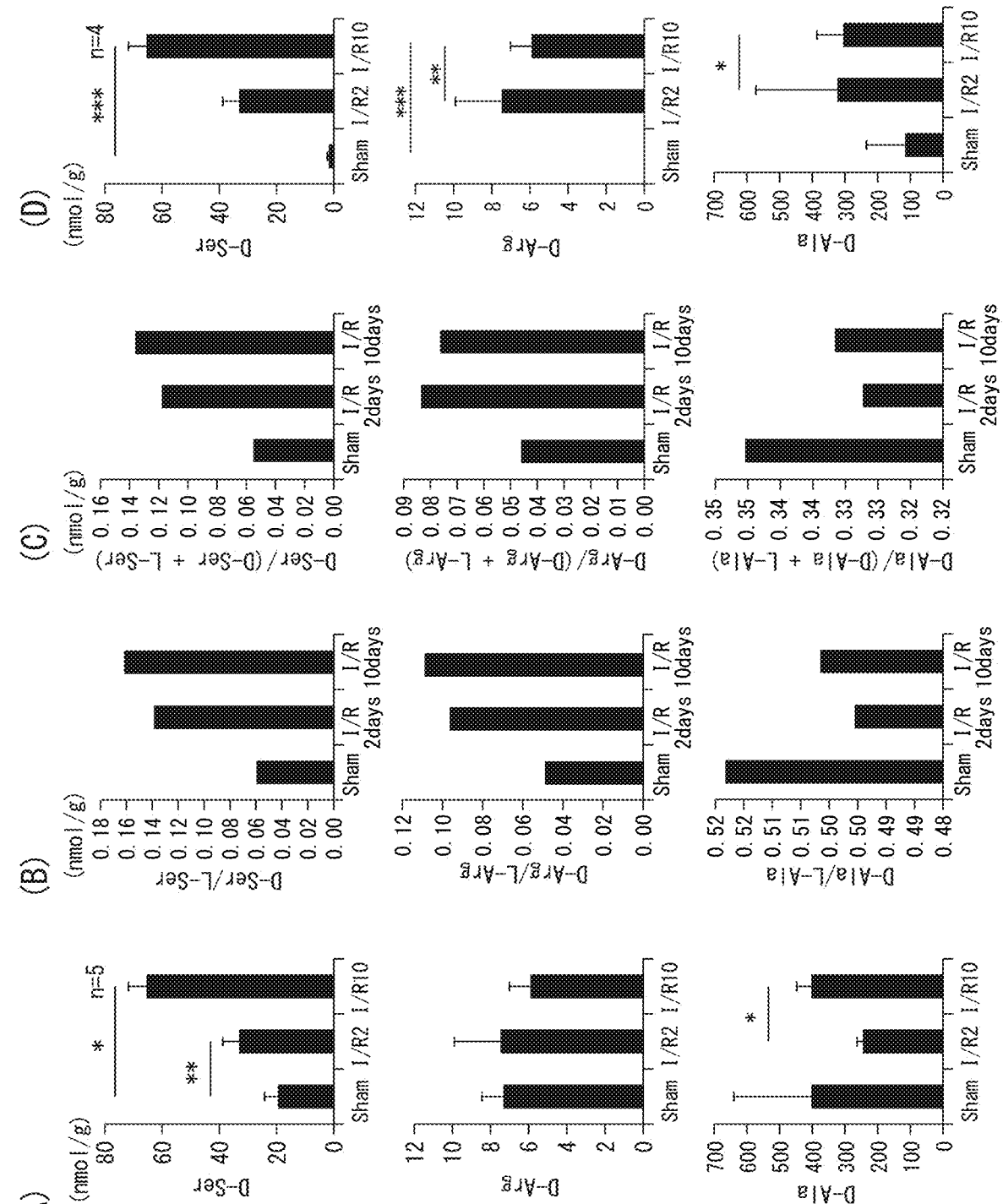
FIG. 4 depicts graphs indicating fluctuations in (A) the amount of D-amino acid, (B) the ratio of D-amino acid/L-amino acid and (C) the ratio of D-amino acid/(D-amino acid+L-amino acid) for serine, arginine and alanine present in feces sampled from mice of a control group (Sham) and mice on days 2 and 10 following induction of a kidney disorder. In addition, FIG. 4(D) indicates fluctuations in the amounts of D-serine, D-arginine and D-alanine in serum.

The results of analyzing changes in the amount of D-amino acids in feces, the ratio of D-form/L-form amino acids and the ratio of the D-form/(D-form+L-form) for serine, arginine and alanine, thought to be particularly useful as markers, are shown in FIGS. 4(A) to 4(C). FIG. 4(D) indicates fluctuations in the serum levels of the D-form of these amino acids for reference purposes.

Relationship Between Intestinal Bacteria and Inflammation

Mice subjected to ischemic reperfusion in the aforementioned mild acute kidney disorder animal model were divided into a wild group housed under normal conditions, a sterile group housed aseptically, and an inoculated group that was inoculated after housing aseptically. Mice housed under normal conditions and then subjected to a sham procedure were used as a control group. The mice were sacrificed on day 2 following induction of ischemic kidney disorder and kidney tissue was recovered. Fixation treatment was carried out on the recovered kidney tissue. Sections were acquired from the fixed kidney tissue followed by PAS staining. F4/80 staining was carried out on other sections. The results of PAS staining are shown in FIG. 5(A). The percentages of necrotic cells were evaluated based on the staining results of FIG. 5(A). Those results are shown in FIG. 5(B). The results of F4/80 staining are shown in FIG. 6(A). The percentages of necrotic cells were evaluated based on the staining results of FIG. 6(A). Those results are shown in the graph of FIG. 6(B).

Changes in Intestinal Bacteria Attributable to Mild Kidney Disorder

Intestinal flora was acquired from the control group (sham) and kidney disorder induction group on post-procedure days 2 and 10 followed by carrying out RAPD-PCR. The results of carrying out electrophoresis on the bands obtained following PCR are shown in FIG. 7(A). In addition, the species and counts of bacteria present were determined by culturing the intestinal flora acquired on post-procedure days 2 and 10 (FIG. 7(B)).

Results

Figure 5:
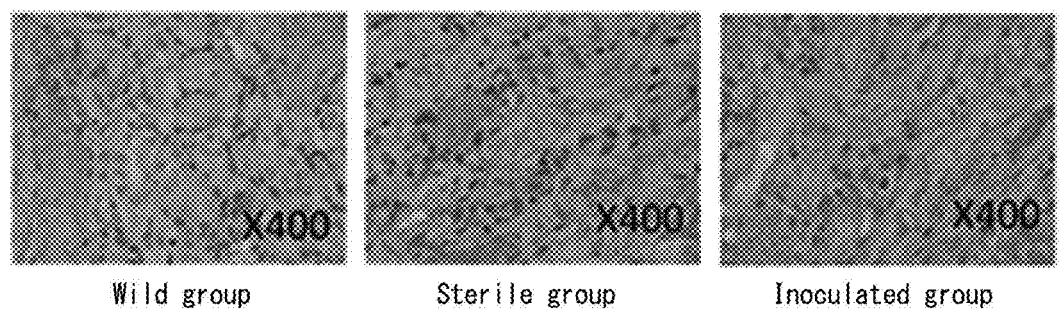
FIG. 5(A) depicts micrographs comparing necrotic cells obtained by PAM staining of the kidneys of mice of a wild group, sterile group and inoculated group following induction of a kidney disorder.
FIG. 5(B) is a graph comparing the results of measuring the percentages of necrotic cells in FIG. 5(A).
Figure 5:
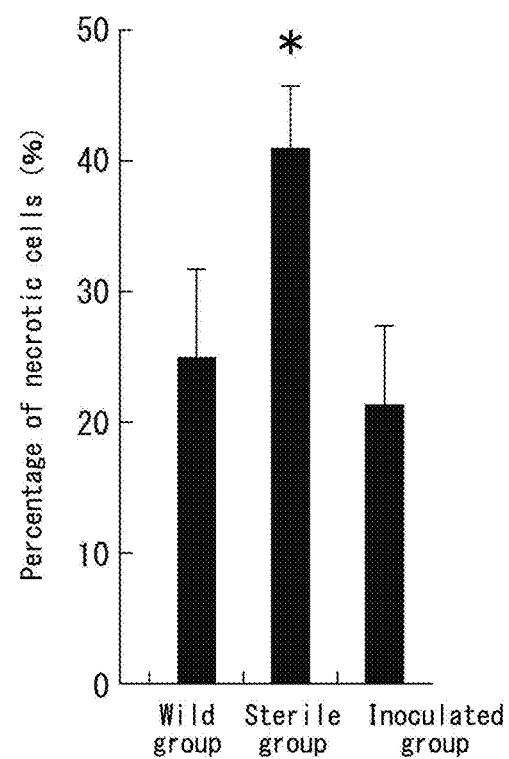
Figure 6:
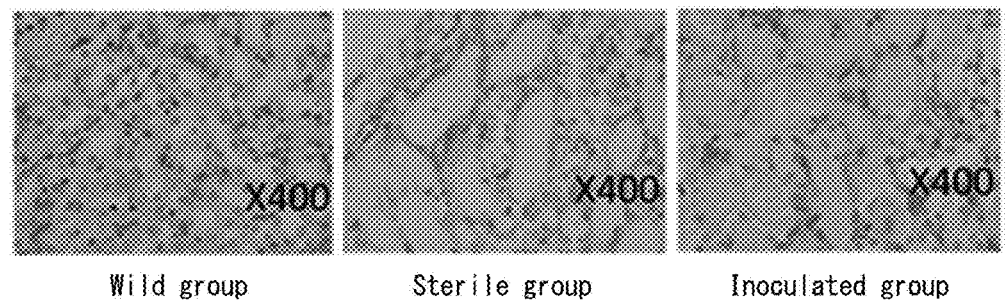
FIG. 6(A) depicts micrographs comparing inflammatory cells (macrophages and monocytes) obtained by F4/80 staining of the kidneys of mice of a wild group, sterile group and inoculated group following induction of a kidney disorder.
FIG. 6(B) is a graph comparing the results of measuring the percentages of inflammatory cells in FIG. 6(A).
Figure 6:
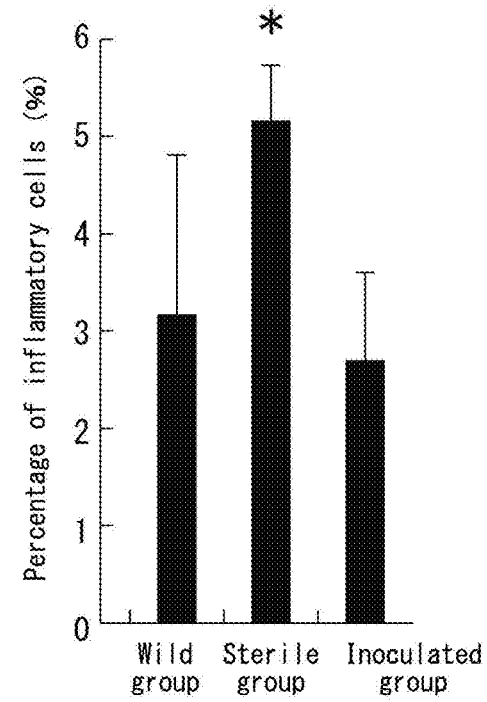

Based on the results shown in FIGS. 5 and 6, although inflammation in response to mild kidney disorder was easily induced in the sterile group, inoculation into the intestine made it possible to reduce inflammation. Thus, there was indicated to be a correlation between intestinal bacteria and inflammation in response to a kidney disorder.

Figure 7:
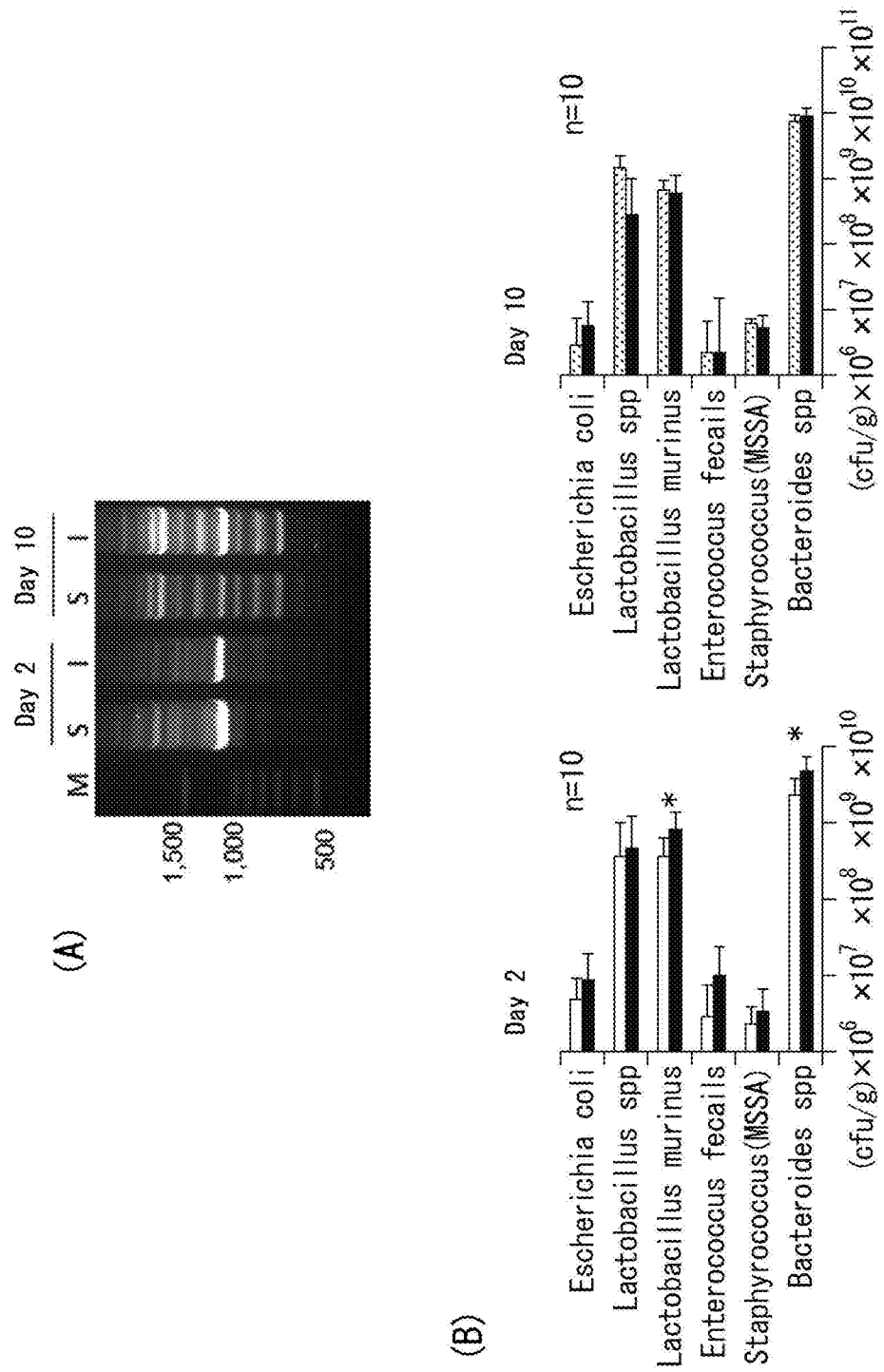
FIG. 7(A) is a diagram showing the results of electrophoresis following fragmentation of intestinal flora DNA on day 2 and day 10 in mice of a kidney disorder induction group.
FIG. 7(B) is a diagram comparing the species and counts of intestinal bacteria in mice on day 2 and day 10 following induction of a kidney disorder.

In FIG. 7, there were changes in the RAPD-PCR band patterns between the wild group that underwent ischemic perfusion and the control group that underwent a sham procedure (FIG. 7(A)), indicating that changes occurred in the counts and/or species of bacteria present. In addition, based on the results shown in FIG. 7(B), counts of a portion of the bacteria changed significantly on post-procedure day 2, and although there were no significant differences on day 10, differences in bacterial counts were indicated to have appeared.

Consequently, the species and counts of intestinal bacteria were indicated to change even in mild kidney disorder. Without intending to be limited by theory, since D-amino acids present in feces are thought to be produced by intestinal bacteria, kidney disorder are thought to cause changes in the counts and species of intestinal bacteria, and as a result thereof, cause changes in the amounts of D-amino acids. Thus, investigating changes in D-amino acids in feces is thought to enable sensitive detection of kidney disorder.

Example 2

Materials and Methods
Research Ethics

The inventors of the present invention acquired stool samples and blood samples from 8 chronic kidney disease patients and 3 healthy subjects at the Kanazawa University Hospital. Informed consent was obtained from the subjects and a study was conducted in accordance with a protocol approved by the Medical Ethics Review Committee of Kanazawa University.

Materials

Amino acid enantiomers and HPLC-grade acetonitrile were purchased from Nacalai Tesque (Kyoto). HPLC-grade methanol, trifluoroacetic acid and boric acid were purchased from Wako Pure Chemical Industries (Osaka). Water was purified using the Milli-Q Gradient A10 System.

Feces samples collected from the 8 chronic kidney disease patients and 3 healthy subjects were dissolved in methanol and introduced into an amino acid enantiomer analysis system according to the D-,L-amine acid simultaneous high sensitivity analysis system developed by Zaitsu, et al (Japanese Patent No. 4291628). Details regarding the analysis conditions for each amino acid are explained in Miyoshi, Y. et al, J. Chromatogr. B, 879: 3184 (2001) and Sasabe, J. et al, Proc. Natl. Acad. Sci. U.S.A., 109: 627 (2012). Briefly speaking, amino acids present in feces were derivatized with 4-fluoro-7-nitro-2,1,3-benzoxadiazole (NBD-F, Tokyo Chemical Industry Co.) and then introduced into an HPLC system (Nanospace SI-2, Shiseido, refer to supplementary information). Briefly speaking, an in-house monolithic ODS column (inner diameter: 0.53 mm×500 mm) was used for the reversed phase separation analytical column. Fluorescence was detected at an excitation wavelength of 470 nm and detection wavelength of 530 nm. Following reversed phase separation, the amino acids were transferred to an optical resolution column. The Sumichiral OA-2500S column (1.5 mm×250 mm, self-packing, packing manufactured by Sumika Chemical Analysis Service Ltd.) using (S)-napthylglycine as chiral selector was used for enantiomer separation. The total amount of amino acid, amount of L-amino acid, amount of D-amino acid, ratio of D-amino acid/L-amino acid and are respectively shown in FIGS. 10(A) to 10(D) for each amino acid.

Serum creatinine levels in blood samples collected from the 8 chronic kidney disease patients and 3 healthy subjects were measured by an enzymatic method. Estimated glomerular filtration rate (eGFR) was determined based on the measured serum creatinine levels and age. The equation used to determine eGFR is as shown below.

$$eGFR = 194 \times \text{Serum creatinine}(SCr)^{-1.094} \times \text{age}^{-0.287} \quad \text{[Equation 1]}$$

(In the equation, the units of age are years, the units of SCr are mg/dL, and the units of glomerular filtration rate (GFR) are mL/min/1.73 $m^2$ of body surface).

Values calculated from the equation were multiplied by a correction factor of 0.739 for women patients.

Correlation coefficients between the eGFR values of the subjects and the total amount of D-amino acid and L-amino acid, amount of L-amino acid, amount of D-amino acid and ratio of D-amino acid/L-amino acid were measured for 20 types of amino acids. The results are shown in FIG. 11.

With respect to the total amount of D-amino acid and L-amino acid, high correlations ($|r|>0.7$) were observed for histidine and allo-threonine, correlations ($|r|>0.4$) were observed for asparagine, arginine, allo-isoleucine and phenylalanine, and low correlations ($|r|>0.2$) were observed for aspartic acid, methionine, valine, isoleucine, leucine, lysine and tyrosine.

With respect to the amount of L-amino acid, a high correlation ($|r|>0.7$) was observed for histidine, correlations ($|r|>0.4$) were observed for asparagine, arginine, phenylalanine and lysine, and low correlations (($|r|>0.2$) were observed for aspartic acid, alanine, methionine, valine, isoleucine, leucine and tyrosine.

With respect to the amount of D-amino acid, high correlations ($|r|>0.7$) were observed for histidine, allo-threonine and lysine, and correlations ($|r|>0.4$) were observed for allo-isoleucine, leucine and phenylalanine.

With respect to the ratio of D-amino acid/L-amino acid, high correlations ($|r|>0.7$) were observed for histidine and lysine, and correlations ($|r|>0.4$) were observed for aspartic acid, alanine, proline, valine and phenylalanine.

Amino acids observed to demonstrate a positive or negative correlation with eGFR can be used as diagnostic markers for kidney failure. A higher correlation indicates greater usefulness in diagnosing kidney failure.

The amount of L-lysine (L-Lys), amount of D-lysine (D-Lys) and ratio of D-lysine/L-lysine (D/L-Lys) were respectively plotted for healthy subjects and chronic kidney disease patients (FIGS. 12(A) to 14(A)). In addition, ROC analyses were carried out based on the amount of L-lysine, amount of D-lysine and ratio of D-lysine/L-lysine for the healthy subjects and chronic kidney disease patients to obtain ROC curves (FIGS. 12(B) to 14(B)). Correlation coefficients were evaluated for the total amount of D-lysine and L-lysine, amount of L-lysine, amount of D-lysine and ratio of D-lysine/L-lysine in the chronic kidney disease patients versus estimated glomerular filtration rate (eGFR) by preparing scatter diagrams (FIGS. 12(C) to 14(C)). Correlation coefficients were also evaluated for the total amount of D-lysine and L-lysine, amount of L-lysine, amount of D-lysine and ratio of D-lysine/L-lysine in the chronic kidney disease patients versus serum creatinine level by preparing scatter diagrams (FIGS. 12(D) to 14(D)).

The correlations of L-Lys with eGFR and serum creatinine level were low (FIGS. 12(C) and 12(D)). In addition, as a result of an ROC analysis of L-Lys relating to diagnosability of chronic kidney disease patients, AUC was determined to be 0.375 and diagnosability was low. The cutoff value thereof was 781.4 nmol/g (FIG. 12(B)).

The correlations of D-Lys with eGFR and serum creatinine level were high (FIGS. 13(C) and 13(D)). In addition, as a result of an ROC analysis of D-Lys relating to diagnosability of chronic kidney disease patients, AUC was determined to be 0.938 and diagnosability was extremely high. The cutoff value thereof was 24.2 nmol/g (FIG. 13(B)).

The correlations of D/L-Lys with eGFR and serum creatinine level were high (FIGS. 14(C) and 14(D)). In addition, as a result of an ROC analysis of D/L-Lys relating to diagnosability of chronic kidney disease patients, AUC was determined to be 0.938 and diagnosability was extremely high. The cutoff value thereof was 24.2 nmol/g (FIG. 14(B)).

Cutoff values can be calculated from the ROC curves, and by making the cutoff value to be 781.4 nmol/g in the case of L-Lys, 24.2 nmol/g in the case of D-Lys, and 24.2 nmol/g in the case of D/L-Lys, chronic kidney disease can be identified with high sensitivity (FIGS. 12(B) to 14(B)).

The invention claimed is:

1. A method for treating a kidney disease, disorder or injury comprising:
   i) measuring the amounts of a D-form and L-form of at least one amino acid among amino acids in a sample of feces or intestinal content;
   ii) calculating a disease-state index value of a kidney disease/injury based on the amount of the D-form, the amount of the L-form, or the amount of the D-form and L-form, of the at least one type of amino acid; and
   iii) correlating a disease-state index value of a kidney disease/injury with the pathology of a kidney disease/injury,
   wherein the disease-state index value of a kidney disease/injury is the ratio of the amount of the D-form to the sum of the amounts of the D-form and the L-form, the ratio of the amount of the L-form to the amount of the D-form, or the ratio of the amount of the D-form to the amount of the L-form, of the at least one type of amino acid, and
   wherein the ratio further determines a treatment plan comprising at least one of dietary guidance, blood pressure management, blood glucose level management, or lipid management.

2. The method according to claim 1, wherein the at least one type of amino acid is selected from the group consisting of serine, glutamic acid, histidine, asparagine, arginine, aspartic acid, allo-threonine, alanine, proline, methionine, valine, allo-isoleucine, isoleucine, leucine, phenylalanine, lysine and tyrosine.

3. The method according to claim 1, wherein the kidney disease or injury is a chronic kidney disease in the case the at least one type of amino acid is selected from the group consisting of histidine, asparagine, arginine, aspartic acid, allo-threonine, alanine, proline, methionine, valine, allo-isoleucine, isoleucine, leucine, phenylalanine, lysine and tyrosine.

4. The method according to claim 3, wherein the at least one type of amino acid is selected from the group consisting of histidine, allo-threonine and lysine.

5. The method according to claim 1, wherein the kidney disease or injury is in the acute stage of a kidney disease or injury or is caused by ischemia in the case the at least one type of amino acid is selected from the group consisting of serine, aspartic acid, glutamic acid, alanine, lysine, arginine and proline.

6. The method according to claim 1, wherein the correlating a disease-state index value of a kidney disease/injury with the pathology of a kidney disease/injury is determined based on a disease-state index reference value determined from the disease-state index values of a healthy subject group and the disease-state index values of a kidney disease/injury patient group.

7. The method according to claim 1, wherein the correlating a disease-state index value of a kidney disease/injury with the pathology of a kidney disease/injury is determined by comparing a target disease-state index value with a cutoff value.

8. The method according to claim 7, wherein the cutoff value is predetermined by an receiver operating characteristic (ROC) curve analysis.

9. The method according to claim 1, further comprising administering to a subject in need thereof the treatment comprising at least one of dietary guidance, blood pressure management, blood glucose level management, or lipid management.

* * * * *